US010227394B2

(12) United States Patent
Chen et al.

(10) Patent No.: US 10,227,394 B2
(45) Date of Patent: Mar. 12, 2019

(54) POLYPEPTIDE COMPOSITIONS WITH TYPE VII COLLAGEN FIBRONECTIN TYPE III-LIKE REPEATS AND TREATMENT METHODS FOR WOUND CLOSURE AND HEALING

(71) Applicant: UNIVERSITY OF SOUTHERN CALIFORNIA, Los Angeles, CA (US)

(72) Inventors: Mei Chen, Altadena, CA (US); David T. Woodley, Altadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/302,453

(22) PCT Filed: Apr. 8, 2015

(86) PCT No.: PCT/US2015/025005
§ 371 (c)(1),
(2) Date: Oct. 6, 2016

(87) PCT Pub. No.: WO2015/157469
PCT Pub. Date: Oct. 15, 2015

(65) Prior Publication Data
US 2017/0015730 A1    Jan. 19, 2017

Related U.S. Application Data

(60) Provisional application No. 61/989,399, filed on May 6, 2014, provisional application No. 61/979,919, filed on Apr. 15, 2014, provisional application No. 61/977,065, filed on Apr. 8, 2014.

(51) Int. Cl.
*A61K 38/17* (2006.01)
*A61K 38/00* (2006.01)
*C07K 14/78* (2006.01)
*A61K 9/00* (2006.01)
*A61K 47/42* (2017.01)

(52) U.S. Cl.
CPC ............ *C07K 14/78* (2013.01); *A61K 9/0014* (2013.01); *A61K 47/42* (2013.01); *A61K 38/00* (2013.01)

(58) Field of Classification Search
None
See application file for complete search history.

(56) References Cited

U.S. PATENT DOCUMENTS

| 2009/0111738 A1 | 4/2009 | Clark et al. |
| 2012/0308537 A1 * | 12/2012 | Chen .................... C12N 5/0654 424/93.21 |
| 2013/0237485 A1 | 9/2013 | Chen et al. |
| 2014/0031295 A1 | 1/2014 | Chen et al. |

FOREIGN PATENT DOCUMENTS

| EP | 2 701 508 A1 | 3/2014 | |
| WO | WO-2008082821 A1 * | 7/2008 | ............. A61K 31/70 |
| WO | WO 2013/020064 A1 | 2/2013 | |

OTHER PUBLICATIONS

Chen et al. 1999. J. Investig Dermatol. 112:177.*
Chen, M, et al.: "*Development and Characterization of a Recombinant Truncated Type VII Collagen Minigene*", Journal of Biological Chemistry, American Society for Biochemistry and Molecular Biology, US, vol. 275, No. 32, Aug. 11, 2000, pp. 24429-24435.
Cogan, J. et al.: "*Type VII collagen binds pro-fibrogenic TGF beta isoforms: Implications for scarring in RDEB Patients and scarless wound healing*"; Journal of Investigative Dermatology, vol. 134, No. Suppl. 1, May 2014, p. S88, & Annual Meeting of the Society-For-Investigative-Dermatology (SID); Albuquerque, NM, USA; May 7-10, 2014. (Abstract).
Jones, Drew A. et al: "*Immunodominant autoepitopes of type VII collagen are short, paired peptide sequences within the fibronectin type III homology region of the noncollagenous (NCI) domain*"; Journal of Investigative Dermatology, vol. 104, No. 2, 1995, pp. 231-235.
Supplemental European Search Report dated Oct. 18, 2017, regarding EP 15 777 144.5.
Wang, X. et al.: "*The absence of functional type VII collagen in RDEB patients causes faculty regulation of TGF-beta and profound skin scarring*"; Journal of Investigative Dermatology, vol. 134, No. Suppl. 1, May 2014, p. S87, XP055413367, & Annual Meeting of the Society-For-Investigative-Dermatology (SID); Albuquerque, NM, USA; May 7-10, 2014. (Abstract).
International Search Report dated Oct. 19, 2015, issued in corresponding application No. PCT/US2015/025005.
Written Opinion of the International Searching Authority dated Oct. 19, 2015, issued in corresponding application No. PCT/US2015/025005.

* cited by examiner

*Primary Examiner* — Shulamith H Shafer
(74) *Attorney, Agent, or Firm* — DLA Piper LLP (US)

(57) ABSTRACT

Disclosed are compositions and methods for accelerating wound closure and preventing inhibiting or reducing scarring or fibrosis. The methods of the present invention include administering to a person in need thereof an effective amount of a pharmaceutical composition comprising collagen 7 and/or one or more functional fragments or variants thereof. The functional fragments generally comprise at least one of the nine Fibronectin Type III-like Region of the NC1 region of collagen 7.

14 Claims, 17 Drawing Sheets

Specification includes a Sequence Listing.

FIG. 6
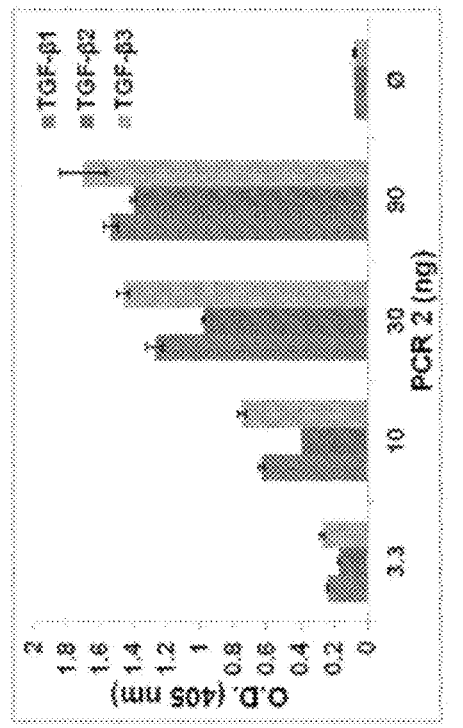
(B)
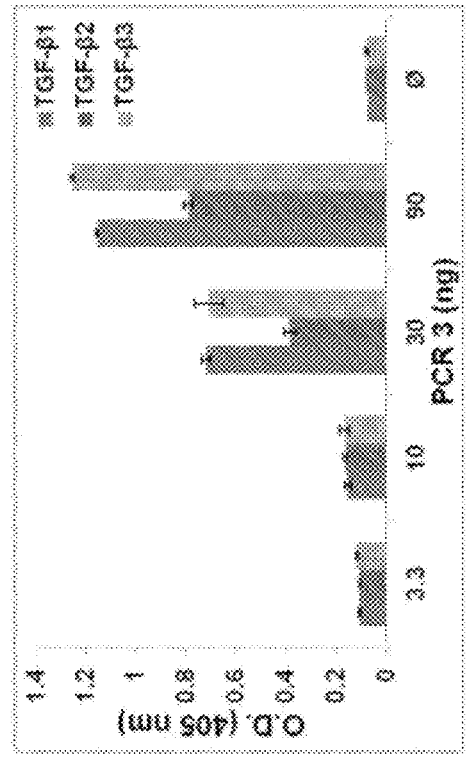
(A)

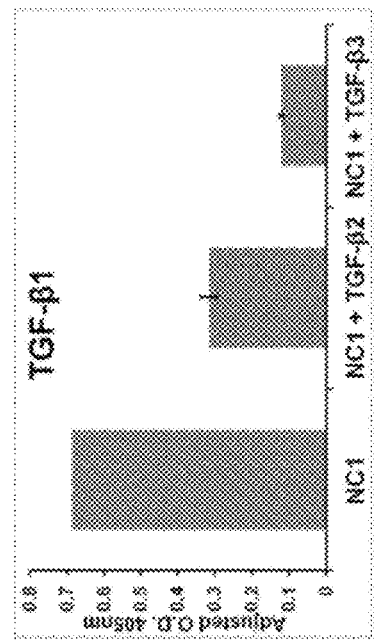
Fig. 13
Fig. 13A Co-IP
Fig. 13B Antigen-to-antigen ELISA

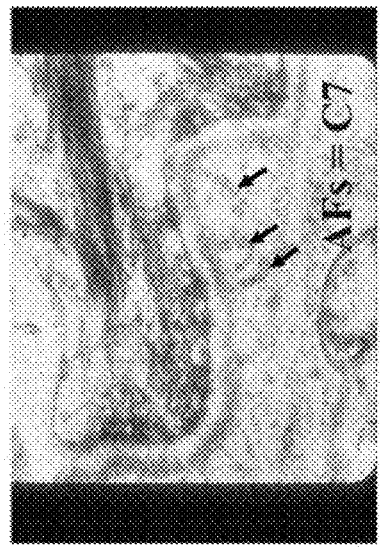
Fig. 14C Normal Skin
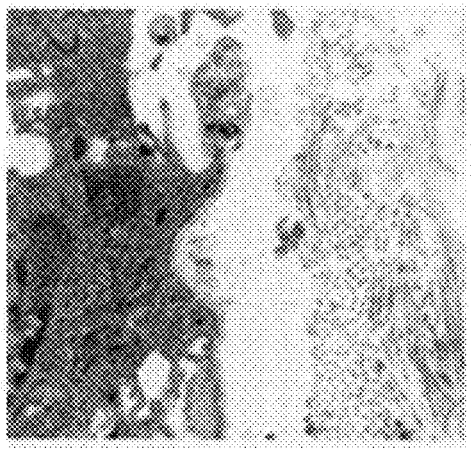
Fig. 14D RDEB Skin
Fig. 14A
Fig. 14B

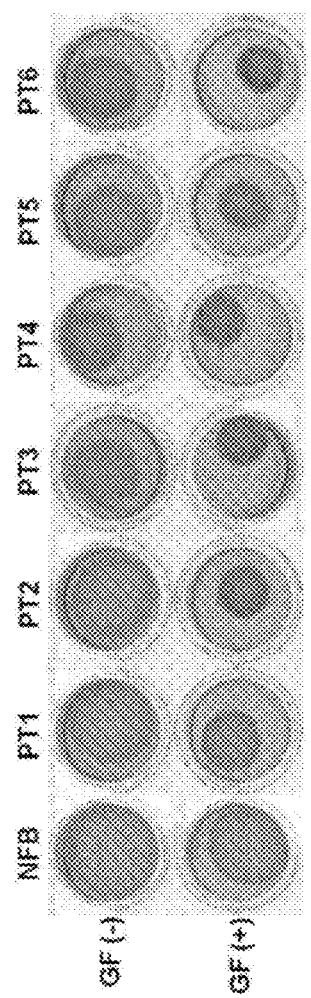
Fig. 16A
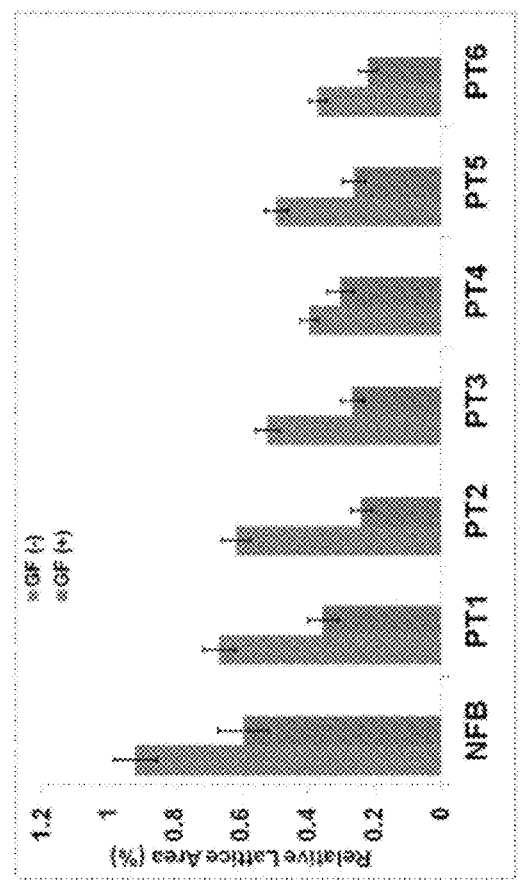
Fig. 16B
Fig. 16

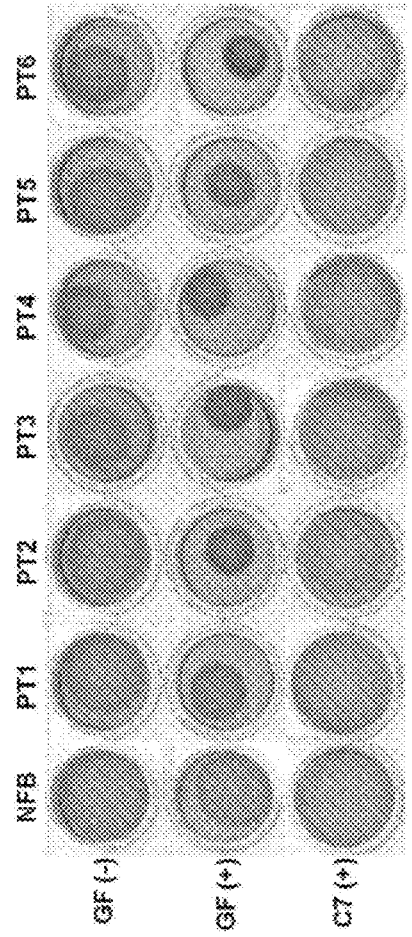
Fig. 17A
Fig. 17B
Fig. 17

SEQUENCE LISTING

<160> NUMBER OF SEQ ID NOS: 1

<210> SEQ ID NO 1
<211> LENGTH: 2944

```
<212> TYPE: PRT
<213> ORGANISM: Homo sapiens

<400> SEQUENCE: 1

Met Thr Leu Arg Leu Leu Val Ala Ala Leu Cys Ala Gly Ile Leu Ala
1               5                   10                  15

Glu Ala Pro Arg Val Arg Ala Gln His Arg Glu Arg Val Thr Cys Thr
            20                  25                  30

Arg Leu Tyr Ala Ala Asp Ile Val Phe Leu Leu Asp Gly Ser Ser Ser
        35                  40                  45

Ile Gly Arg Ser Asn Phe Arg Glu Val Arg Ser Phe Leu Glu Gly Leu
    50                  55                  60

Val Leu Pro Phe Ser Gly Ala Ala Ser Ala Gln Gly Val Arg Phe Ala
65                  70                  75                  80

Thr Val Gln Tyr Ser Asp Asp Pro Arg Thr Glu Phe Gly Leu Asp Ala
                85                  90                  95

Leu Gly Ser Gly Gly Asp Val Ile Arg Ala Ile Arg Glu Leu Ser Tyr
            100                 105                 110

Lys Gly Gly Asn Thr Arg Thr Gly Ala Ala Ile Leu His Val Ala Asp
        115                 120                 125

His Val Phe Leu Pro Gln Leu Ala Arg Pro Gly Val Pro Lys Val Cys
130                 135                 140

Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
    290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
            340                 345                 350

Ala Thr Gly Tyr Arg Val Thr Trp Arg Val Leu Ser Gly Gly Pro Thr
        355                 360                 365

Gln Gln Gln Glu Leu Gly Pro Gly Gln Gly Ser Val Leu Leu Arg Asp
    370                 375                 380

Leu Glu Pro Gly Thr Asp Tyr Glu Val Thr Val Ser Thr Leu Phe Gly
385                 390                 395                 400
```

```
Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
        435                 440                 445

Arg Arg Glu Thr Gly Leu Glu Pro Pro Gln Lys Val Val Leu Pro Ser
    450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
        515                 520                 525

Ser Pro Val Pro Gly Ala Thr Gln Tyr Arg Ile Ile Val Arg Ser Thr
    530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
        595                 600                 605

Ser Asp Ala Thr Arg Val Arg Val Ala Trp Gly Pro Val Pro Gly Ala
610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
        675                 680                 685

Val Arg Thr Val His Val Thr Gln Ala Ser Ser Ser Val Thr Ile
    690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750

Val Arg Ala His Val Ala Gly Val Asp Gly Pro Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815
```

-continued

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
            835                 840                 845

Gly Asp Arg Glu Gly Thr Pro Val Ser Ile Val Val Thr Thr Pro Pro
850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
            885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
            915                 920                 925

Gln Tyr Arg Val Arg Leu Ser Val Leu Gly Pro Ala Gly Glu Gly Pro
            930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
            965                 970                 975

Thr Pro Val Ser Arg Ala Ser Ser Tyr Ile Leu Ser Trp Arg Pro Leu
            980                 985                 990

Arg Gly Pro Gly Gln Glu Val Pro Gly Ser Pro Gln Thr Leu Pro Gly
            995                 1000                1005

Ile Ser Ser Ser Gln Arg Val Thr Gly Leu Glu Pro Gly Val Ser
1010                1015                1020

Tyr Ile Phe Ser Leu Thr Pro Val Leu Asp Gly Val Arg Gly Pro
1025                1030                1035

Glu Ala Ser Val Thr Gln Thr Pro Val Cys Pro Arg Gly Leu Ala
1040                1045                1050

Asp Val Val Phe Leu Pro His Ala Thr Gln Asp Asn Ala His Arg
1055                1060                1065

Ala Glu Ala Thr Arg Arg Val Leu Glu Arg Leu Val Leu Ala Leu
1070                1075                1080

Gly Pro Leu Gly Pro Gln Ala Val Gln Val Gly Leu Leu Ser Tyr
1085                1090                1095

Ser His Arg Pro Ser Pro Leu Phe Pro Leu Asn Gly Ser His Asp
1100                1105                1110

Leu Gly Ile Ile Leu Gln Arg Ile Arg Asp Met Pro Tyr Met Asp
1115                1120                1125

Pro Ser Gly Asn Asn Leu Gly Thr Ala Val Val Thr Ala His Arg
1130                1135                1140

Tyr Met Leu Ala Pro Asp Ala Pro Gly Arg Arg Gln His Val Pro
1145                1150                1155

Gly Val Met Val Leu Leu Val Asp Glu Pro Leu Arg Gly Asp Ile
1160                1165                1170

Phe Ser Pro Ile Arg Glu Ala Gln Ala Ser Gly Leu Asn Val Val
1175                1180                1185

Met Leu Gly Met Ala Gly Ala Asp Pro Glu Gln Leu Arg Arg Leu
1190                1195                1200

Ala Pro Gly Met Asp Ser Val Gln Thr Phe Phe Ala Val Asp Asp
1205                1210                1215

Gly Pro Ser Leu Asp Gln Ala Val Ser Gly Leu Ala Thr Ala Leu

```
            1220                1225                1230
Cys Gln Ala Ser Phe Thr Thr Gln Pro Arg Pro Glu Pro Cys Pro
            1235                1240                1245

Val Tyr Cys Pro Lys Gly Gln Lys Gly Glu Pro Gly Glu Met Gly
            1250                1255                1260

Leu Arg Gly Gln Val Gly Pro Pro Gly Asp Pro Gly Leu Pro Gly
            1265                1270                1275

Arg Thr Gly Ala Pro Gly Pro Gln Gly Pro Pro Gly Ser Ala Thr
            1280                1285                1290

Ala Lys Gly Glu Arg Gly Phe Pro Gly Ala Asp Gly Arg Pro Gly
            1295                1300                1305

Ser Pro Gly Arg Ala Gly Asn Pro Gly Thr Pro Gly Ala Pro Gly
            1310                1315                1320

Leu Lys Gly Ser Pro Gly Leu Pro Gly Pro Arg Gly Asp Pro Gly
            1325                1330                1335

Glu Arg Gly Pro Arg Gly Pro Lys Gly Glu Pro Gly Ala Pro Gly
            1340                1345                1350

Gln Val Ile Gly Gly Glu Gly Pro Gly Leu Pro Gly Arg Lys Gly
            1355                1360                1365

Asp Pro Gly Pro Ser Gly Pro Pro Gly Pro Arg Gly Pro Leu Gly
            1370                1375                1380

Asp Pro Gly Pro Arg Gly Pro Pro Gly Leu Pro Gly Thr Ala Met
            1385                1390                1395

Lys Gly Asp Lys Gly Asp Arg Gly Glu Arg Gly Pro Pro Gly Pro
            1400                1405                1410

Gly Glu Gly Gly Ile Ala Pro Gly Glu Pro Gly Leu Pro Gly Leu
            1415                1420                1425

Pro Gly Ser Pro Gly Pro Gln Gly Pro Val Gly Pro Pro Gly Lys
            1430                1435                1440

Lys Gly Glu Lys Gly Asp Ser Glu Asp Gly Ala Pro Gly Leu Pro
            1445                1450                1455

Gly Gln Pro Gly Ser Pro Gly Glu Gln Gly Pro Arg Gly Pro Pro
            1460                1465                1470

Gly Ala Ile Gly Pro Lys Gly Asp Arg Gly Phe Pro Gly Pro Leu
            1475                1480                1485

Gly Glu Ala Gly Glu Lys Gly Glu Arg Gly Pro Pro Gly Pro Ala
            1490                1495                1500

Gly Ser Arg Gly Leu Pro Gly Val Ala Gly Arg Pro Gly Ala Lys
            1505                1510                1515

Gly Pro Glu Gly Pro Pro Gly Pro Thr Gly Arg Gln Gly Glu Lys
            1520                1525                1530

Gly Glu Pro Gly Arg Pro Gly Asp Pro Ala Val Val Gly Pro Ala
            1535                1540                1545

Val Ala Gly Pro Lys Gly Glu Lys Gly Asp Val Gly Pro Ala Gly
            1550                1555                1560

Pro Arg Gly Ala Thr Gly Val Gln Gly Glu Arg Gly Pro Pro Gly
            1565                1570                1575

Leu Val Leu Pro Gly Asp Pro Gly Pro Lys Gly Asp Pro Gly Asp
            1580                1585                1590

Arg Gly Pro Ile Gly Leu Thr Gly Arg Ala Gly Pro Pro Gly Asp
            1595                1600                1605

Ser Gly Pro Pro Gly Glu Lys Gly Asp Pro Gly Arg Pro Gly Pro
            1610                1615                1620
```

```
Pro Gly Pro Val Gly Pro Arg Gly Arg Asp Gly Glu Val Gly Glu
    1625            1630                1635
Lys Gly Asp Glu Gly Pro Gly Asp Pro Gly Leu Pro Gly Lys
    1640            1645                1650
Ala Gly Glu Arg Gly Leu Arg Gly Ala Pro Gly Val Arg Gly Pro
    1655            1660                1665
Val Gly Glu Lys Gly Asp Gln Gly Asp Pro Gly Glu Asp Gly Arg
    1670            1675                1680
Asn Gly Ser Pro Gly Ser Ser Gly Pro Lys Gly Asp Arg Gly Glu
    1685            1690                1695
Pro Gly Pro Pro Gly Pro Pro Gly Arg Leu Val Asp Thr Gly Pro
    1700            1705                1710
Gly Ala Arg Glu Lys Gly Glu Pro Gly Asp Arg Gly Gln Glu Gly
    1715            1720                1725
Pro Arg Gly Pro Lys Gly Asp Pro Gly Leu Pro Gly Ala Pro Gly
    1730            1735                1740
Glu Arg Gly Ile Glu Gly Phe Arg Gly Pro Pro Gly Pro Gln Gly
    1745            1750                1755
Asp Pro Gly Val Arg Gly Pro Ala Gly Glu Lys Gly Asp Arg Gly
    1760            1765                1770
Pro Pro Gly Leu Asp Gly Arg Ser Gly Leu Asp Gly Lys Pro Gly
    1775            1780                1785
Ala Ala Gly Pro Ser Gly Pro Asn Gly Ala Ala Gly Lys Ala Gly
    1790            1795                1800
Asp Pro Gly Arg Asp Gly Leu Pro Gly Leu Arg Gly Glu Gln Gly
    1805            1810                1815
Leu Pro Gly Pro Ser Gly Pro Pro Gly Leu Pro Gly Lys Pro Gly
    1820            1825                1830
Glu Asp Gly Lys Pro Gly Leu Asn Gly Lys Asn Gly Glu Pro Gly
    1835            1840                1845
Asp Pro Gly Glu Asp Gly Arg Lys Gly Glu Lys Gly Asp Ser Gly
    1850            1855                1860
Ala Ser Gly Arg Glu Gly Arg Asp Gly Pro Lys Gly Glu Arg Gly
    1865            1870                1875
Ala Pro Gly Ile Leu Gly Pro Gln Gly Pro Pro Gly Leu Pro Gly
    1880            1885                1890
Pro Val Gly Pro Pro Gly Gln Gly Phe Pro Gly Val Pro Gly Gly
    1895            1900                1905
Thr Gly Pro Lys Gly Asp Arg Gly Glu Thr Gly Ser Lys Gly Glu
    1910            1915                1920
Gln Gly Leu Pro Gly Glu Arg Gly Leu Arg Gly Glu Pro Gly Ser
    1925            1930                1935
Val Pro Asn Val Asp Arg Leu Leu Glu Thr Ala Gly Ile Lys Ala
    1940            1945                1950
Ser Ala Leu Arg Glu Ile Val Glu Thr Trp Asp Glu Ser Ser Gly
    1955            1960                1965
Ser Phe Leu Pro Val Pro Glu Arg Arg Arg Gly Pro Lys Gly Asp
    1970            1975                1980
Ser Gly Glu Gln Gly Pro Pro Gly Lys Glu Gly Pro Ile Gly Phe
    1985            1990                1995
Pro Gly Glu Arg Gly Leu Lys Gly Asp Arg Gly Asp Pro Gly Pro
    2000            2005                2010
```

-continued

Gln Gly Pro Pro Gly Leu Ala Leu Gly Glu Arg Gly Pro Pro Gly
2015                2020                2025

Pro Ser Gly Leu Ala Gly Glu Pro Gly Lys Pro Gly Ile Pro Gly
2030                2035                2040

Leu Pro Gly Arg Ala Gly Gly Val Gly Glu Ala Gly Arg Pro Gly
2045                2050                2055

Glu Arg Gly Glu Arg Gly Glu Lys Gly Glu Arg Gly Glu Gln Gly
2060                2065                2070

Arg Asp Gly Pro Pro Gly Leu Pro Gly Thr Pro Gly Pro Pro Gly
2075                2080                2085

Pro Pro Gly Pro Lys Val Ser Val Asp Glu Pro Gly Pro Gly Leu
2090                2095                2100

Ser Gly Glu Gln Gly Pro Pro Gly Leu Lys Gly Ala Lys Gly Glu
2105                2110                2115

Pro Gly Ser Asn Gly Asp Gln Gly Pro Lys Gly Asp Arg Gly Val
2120                2125                2130

Pro Gly Ile Lys Gly Asp Arg Gly Glu Pro Gly Pro Arg Gly Gln
2135                2140                2145

Asp Gly Asn Pro Gly Leu Pro Gly Glu Arg Gly Met Ala Gly Pro
2150                2155                2160

Glu Gly Lys Pro Gly Leu Gln Gly Pro Arg Gly Pro Pro Gly Pro
2165                2170                2175

Val Gly Gly His Gly Asp Pro Gly Pro Pro Gly Ala Pro Gly Leu
2180                2185                2190

Ala Gly Pro Ala Gly Pro Gln Gly Pro Ser Gly Leu Lys Gly Glu
2195                2200                2205

Pro Gly Glu Thr Gly Pro Pro Gly Arg Gly Leu Thr Gly Pro Thr
2210                2215                2220

Gly Ala Val Gly Leu Pro Gly Pro Pro Gly Pro Ser Gly Leu Val
2225                2230                2235

Gly Pro Gln Gly Ser Pro Gly Leu Pro Gly Gln Val Gly Glu Thr
2240                2245                2250

Gly Lys Pro Gly Ala Pro Gly Arg Asp Gly Ala Ser Gly Lys Asp
2255                2260                2265

Gly Asp Arg Gly Ser Pro Gly Val Pro Gly Ser Pro Gly Leu Pro
2270                2275                2280

Gly Pro Val Gly Pro Lys Gly Glu Pro Gly Pro Thr Gly Ala Pro
2285                2290                2295

Gly Gln Ala Val Val Gly Leu Pro Gly Ala Lys Gly Glu Lys Gly
2300                2305                2310

Ala Pro Gly Gly Leu Ala Gly Asp Leu Val Gly Glu Pro Gly Ala
2315                2320                2325

Lys Gly Asp Arg Gly Leu Pro Gly Pro Arg Gly Glu Lys Gly Glu
2330                2335                2340

Ala Gly Arg Ala Gly Glu Pro Gly Asp Pro Gly Glu Asp Gly Gln
2345                2350                2355

Lys Gly Ala Pro Gly Pro Lys Gly Phe Lys Gly Asp Pro Gly Val
2360                2365                2370

Gly Val Pro Gly Ser Pro Gly Pro Pro Gly Pro Pro Gly Val Lys
2375                2380                2385

Gly Asp Leu Gly Leu Pro Gly Leu Pro Gly Ala Pro Gly Val Val
2390                2395                2400

Gly Phe Pro Gly Gln Thr Gly Pro Arg Gly Glu Met Gly Gln Pro

-continued

```
            2405                2410                2415
Gly Pro Ser Gly Glu Arg Gly Leu Ala Gly Pro Pro Gly Arg Glu
        2420                2425                2430
Gly Ile Pro Gly Pro Leu Gly Pro Pro Gly Pro Pro Gly Ser Val
        2435                2440                2445
Gly Pro Pro Gly Ala Ser Gly Leu Lys Gly Asp Lys Gly Asp Pro
        2450                2455                2460
Gly Val Gly Leu Pro Gly Pro Arg Gly Glu Arg Gly Glu Pro Gly
        2465                2470                2475
Ile Arg Gly Glu Asp Gly Arg Pro Gly Gln Glu Gly Pro Arg Gly
        2480                2485                2490
Leu Thr Gly Pro Pro Gly Ser Arg Gly Glu Arg Gly Glu Lys Gly
        2495                2500                2505
Asp Val Gly Ser Ala Gly Leu Lys Gly Asp Lys Gly Asp Ser Ala
        2510                2515                2520
Val Ile Leu Gly Pro Pro Gly Pro Arg Gly Ala Lys Gly Asp Met
        2525                2530                2535
Gly Glu Arg Gly Pro Arg Gly Leu Asp Gly Asp Lys Gly Pro Arg
        2540                2545                2550
Gly Asp Asn Gly Asp Pro Gly Asp Lys Gly Ser Lys Gly Glu Pro
        2555                2560                2565
Gly Asp Lys Gly Ser Ala Gly Leu Pro Gly Leu Arg Gly Leu Leu
        2570                2575                2580
Gly Pro Gln Gly Gln Pro Gly Ala Ala Gly Ile Pro Gly Asp Pro
        2585                2590                2595
Gly Ser Pro Gly Lys Asp Gly Val Pro Gly Ile Arg Gly Glu Lys
        2600                2605                2610
Gly Asp Val Gly Phe Met Gly Pro Arg Gly Leu Lys Gly Glu Arg
        2615                2620                2625
Gly Val Lys Gly Ala Cys Gly Leu Asp Gly Glu Lys Gly Asp Lys
        2630                2635                2640
Gly Glu Ala Gly Pro Pro Gly Arg Pro Gly Leu Ala Gly His Lys
        2645                2650                2655
Gly Glu Met Gly Glu Pro Gly Val Pro Gly Gln Ser Gly Ala Pro
        2660                2665                2670
Gly Lys Glu Gly Leu Ile Gly Pro Lys Gly Asp Arg Gly Phe Asp
        2675                2680                2685
Gly Gln Pro Gly Pro Lys Gly Asp Gln Gly Glu Lys Gly Glu Arg
        2690                2695                2700
Gly Thr Pro Gly Ile Gly Gly Phe Pro Gly Pro Ser Gly Asn Asp
        2705                2710                2715
Gly Ser Ala Gly Pro Pro Gly Pro Pro Gly Ser Val Gly Pro Arg
        2720                2725                2730
Gly Pro Glu Gly Leu Gln Gly Gln Lys Gly Glu Arg Gly Pro Pro
        2735                2740                2745
Gly Glu Arg Val Val Gly Ala Pro Gly Val Pro Gly Ala Pro Gly
        2750                2755                2760
Glu Arg Gly Glu Gln Gly Arg Pro Gly Pro Ala Gly Pro Arg Gly
        2765                2770                2775
Glu Lys Gly Glu Ala Ala Leu Thr Glu Asp Asp Ile Arg Gly Phe
        2780                2785                2790
Val Arg Gln Glu Met Ser Gln His Cys Ala Cys Gln Gly Gln Phe
        2795                2800                2805
```

-continued

```
Ile Ala Ser Gly Ser Arg Pro Leu Pro Ser Tyr Ala Ala Asp Thr
2810                2815            2820

Ala Gly Ser Gln Leu His Ala Val Pro Val Leu Arg Val Ser His
2825                2830            2835

Ala Glu Glu Glu Arg Val Pro Pro Glu Asp Asp Glu Tyr Ser
2840                2845            2850

Glu Tyr Ser Glu Tyr Ser Val Glu Glu Tyr Gln Asp Pro Glu Ala
2855                2860            2865

Pro Trp Asp Ser Asp Asp Pro Cys Ser Leu Pro Leu Asp Glu Gly
2870                2875            2880

Ser Cys Thr Ala Tyr Thr Leu Arg Trp Tyr His Arg Ala Val Thr
2885                2890            2895

Gly Ser Thr Glu Ala Cys His Pro Phe Val Tyr Gly Gly Cys Gly
2900                2905            2910

Gly Asn Ala Asn Arg Phe Gly Thr Arg Glu Ala Cys Glu Arg Arg
2915                2920            2925

Cys Pro Pro Arg Val Val Gln Ser Gln Gly Thr Gly Thr Ala Gln
2930                2935            2940

Asp
```

POLYPEPTIDE COMPOSITIONS WITH TYPE VII COLLAGEN FIBRONECTIN TYPE III-LIKE REPEATS AND TREATMENT METHODS FOR WOUND CLOSURE AND HEALING

RELATED APPLICATIONS

This application is a National Stage Application which claims priority to PCT/US2015/025005, filed Apr. 8, 2015, which claims priority to U.S. Provisional Application Ser. No. 61/989,399, filed on May 6, 2014, U.S. Provisional Application Ser. No. 61/979,919, filed on Apr. 15, 2014 and U.S. Provisional Application Ser. No. 61/977,065, filed on Apr. 8, 2014, the entire contents of which are incorporated herein by reference in their entirety.

STATEMENT REGARDING FEDERALLY FUNDED RESEARCH

This invention was made with government support under Grant Nos. RO1 AR47981 and AR33625 awarded by National Institute of Health. The government has certain rights in the invention.

INCORPORATION OF SEQUENCE LISTING

The material in the accompanying sequence listing is hereby incorporated by reference into this application. The accompanying sequence listing text file, name 374634_000688_Sequence_Listing.txt, was created on Mar. 19, 2018, and is 10 kb. The file can be assessed using Microsoft Word on a computer that uses Windows OS.

BACKGROUND

Type VII collagen (Collagen 7) is the major component of anchoring fibrils, attachment structures within the basement membrane zone (BMZ) between the epidermis and dermis of human skin. Genetic defects in the Collagen 7 gene result in dystrophic epidermolysis bullosa (DEB), diseases characterized by generalized blistering and skin fragility.

Collagen 7 is composed of three identical alpha chains, each consisting of a 145 kDa central collagenous triple-helical segment (TH), flanked by a large globular 145 kDa amino-terminal non-collagenous domain (NC1), and a smaller 34 kDa carboxyl-terminal non-collagenous domain (NC2). Sequence analysis of NC1 reveals multiple submodules with homology to known adhesive molecules, such as cartilage matrix protein (CMP), nine fibronectin type III-like repeats (FNIII), and the A domain of von Willebrand factor (VWF-A). The very adhesive NC1 domain may facilitate binding of Collagen 7 to other BMZ and extracellular matrix components (ECM). These associations may stabilize Collagen 7 molecular aggregations and adhesion of the BMZ to the dermis. Therefore, structural alterations in Collagen 7 are likely to result in functional disruption in its interactions with ECM components and epidermal-dermal disadherance, as seen in DEB.

TGF-β has been shown to bind to various ECM proteins such as fibronectin, type IV collagen and tenascin as well as a number of small interstitial proteoglycans such as biglycan, decorin and fibromodulin. This matrix binding may regulate TGF-beta activities by sequestering TGF-beta into extracellular matrix and inhibiting its fibrotic properties. Fibronectin type III like repeats (FNII) within fibronectin and tenascin are responsible for their binding to TGFβ.

As shown in FIGS. 14A and 14B, patients with RDEB often suffer severe scarring and fibrotic mitten deformities that are characteristic. Aggressive and usually fatal skin cancers develop in areas of scarring and chronic wounds that frequently took the patients' life. These children have a gene defect in the COLA1 gene leading to abnormal type VII collagen, the major component of anchoring fibrils. As electron micrograph of normal human skin in FIG. 14C, these are large structures located that the dermal-epidermal junction and function to hold the epidermis and dermis together. The electron micrograph of RDEB skin in FIG. 14D shows a paucity of anchoring fibrils and clear epidermal-dermal separation.

BRIEF SUMMARY

Type VII collagen (Collagen 7) was once thought to be a collagen in the skin that formed anchoring fibril structures and adhered the epidermis and dermis of skin together. We have found that type VII collagen in healing skin wounds is not limited to anchoring fibril structures, but rather is diffusely distributed in the neodermis where it promotes wound closure and inhibits wound scarring.

One aspect of the present invention is the finding that Collagen 7 prevents skin scarring, by binding to TGF-β1 and inhibiting profibrogenic TGF-β1 and TGF-β2 activity. Further, our data show that Collagen 7 inhibits the contraction of collagen lattices, an in vitro assay that correlates with clinical scarring. These findings provide a molecular basis for the therapeutic use of Collagen 7 or its functional fragments where excessive TGF-β activity causes scarring and fibrosis such as in recessive dystrophic epidermolysis bullosa (RDEB) and hypertrophic burn scars.

Treatment methods according to the present invention involving the administration of collagen 7, its functional fragments as defined herein, and variants may generally be employed when it is clinically desirable to either (i) accelerate wound closure, or (ii) prevent, inhibit or reduce scarring or fibrosis. While not being limited to theory, it is believed that these effects are achieved, at least in part, via binding to and decreasing pro-fibrogenic TGF-β activities.

One embodiment of the present invention is directed to a pharmaceutical composition comprising Collagen 7, or a functional fragment or variant thereof as defined herein, and one or more pharmaceutically acceptable carriers, for use in treating a subject in need of accelerated wound closure, at risk for developing scarring or fibrosis or in connection with treatments for existing scars or fibrosis. Treatment methods according to this embodiment comprises administering to a patient in need thereof an effective amount of C7 and/or one or more functional fragments or variant thereof.

In one embodiment, the subject to be treated is a person having dystrophic epidermolysis bullosa (EB), which is caused by mutations in the COL7A1 gene, the gene which encodes for the protein Collagen 7. In this embodiment, it is preferably topically administered. In another embodiment, the subject to be treated is a, subject such as a human, having no mutation in the COL7A1 gene, i.e. a person without EB. Numerous clinical indications are associated with scarring and fibrosis in persons without EB, including keloids and hypertrophic scars in the skin, tendon adhesions, transmission blockage following nerve injury, scleroderma, Crohn's disease, esophageal strictures, urethral strictures, capsules around breast implants, liver cirrhosis, atherosclerosis and fibrotic non-union in bone. Hypertrophic scars or keloids may form, for instance, as a result of injury, including burns, surgery and acne. It should be noted that a person with EB may be at risk for fibrosis or scarring resulting from these same clinical indications and can likewise benefit from treatments according to the present invention even when treatment with collagen 7 is not indicated as a separate treatment for EB.

Another aspect of the present invention is directed to functional fragments of Collagen 7 and variants thereof, preferably isolated functional fragments and variants thereof and pharmaceutical compositions, and treatment methods based thereon. As used herein, a functional fragment of Collagen 7 refers to a portion of Collagen 7 that maintains the ability to bind to TGF-β1 and inhibit profibrogenic TGF-β1 and TGF-β2 activity but does not include the entirety of Collagen 7's 2,944 amino acid residues (SEQ ID NO:1). Optionally, the functional fragment may be sized and constructed so that it does not retain an ability to form anchoring fibrils between the epidermal and epidermal layers of human skin but nonetheless maintains the ability to bind to TGF-β1 and inhibit profibrogenic TGF-β1 and TGF-β2 activity.

The functional fragments may be formulated as pharmaceutical compositions and used in connection with treatment methods based on the administration of the selected functional fragment or and/or variants thereof. These methods, as described herein, include methods for accelerating wound closure, or inhibiting or reducing fibrosis and/or scarring by administering an effective amount of a pharmaceutical composition comprising the selected functional fragment and/or variants thereof.

The functional fragments of the present invention generally comprise at least one of the nine fibronectin type III-like repeats ("FNIII") of Collagen 7's NC1 region. In one embodiment, the functional fragment includes all of the NC1 domain of Collagen 7, i.e. it includes the entire non-collagenous NC1 domain (i.e. residues 17-1253 in the mature peptide (of SEQ ID NO:1)). Thus, one embodiment of the invention is an isolated polypeptide comprising an amino acid sequence corresponding the entire NC1 region or variants thereof.

In another embodiment, the functional fragment is a polypeptide that includes at least one of the FNIII Region 1, FNIII Region 5 and FNIII Region 6. Thus, one embodiment of the present invention is an isolated polypeptide comprising an amino acid sequence corresponding to FNIII Region 1 or a variant thereof and optionally, an amino acid sequence corresponding to FNIII Region 5 and/or FNIII Region 6 or a variant thereof.

Another embodiment of the present invention is an isolated polypeptide comprising an amino acid sequence corresponding to FNIII Region 5 or a variant thereof and optionally, an amino acid sequence corresponding to FNIII Region 6 or a variant thereof. Another embodiment of the present invention is an isolated polypeptide comprising an amino acid sequence corresponding to FNIII Region 6 or a variant thereof.

Another embodiment of the present invention is an isolated polypeptide comprising an amino acid sequence corresponding to PCR1 or a variant thereof.

Another embodiment of the present invention is an isolated polypeptide comprising an amino acid sequence corresponding to PCR2 or a variant thereof.

Another embodiment of the present invention is an isolated polypeptide comprising an amino acid sequence corresponding to PCR3 or a variant thereof.

Another embodiment of the present invention is an isolated polypeptide comprising an amino acid sequence corresponding to PpuMI or a variant thereof.

Another embodiment of the present invention is an isolated polypeptide comprising an amino acid sequence corresponding to FP15 or a variant thereof.

Another embodiment of the present invention is an isolated polypeptide comprising an amino acid sequence corresponding to FP16 or a variant thereof.

BRIEF DESCRIPTION OF THE FIGURES

FIG. 6 shows the dose-dependent Binding of NC1 Subdomains to all three TGF-β isoforms.

FIGS. 11A and 11B show that C7 Binds More Strongly to TGF-β Than Fibronectin. Fibronectin is also known to bind to TGF beta isoforms. FIG. 11B shows Coomassive Blue stained 6% SDS-PAGE slab gel of the purified recombinant NC1, fibronectin and C7 used in this experiment.

As shown in FIGS. 12A and 12B rC7 and NC1 retain the ability to bind to TGF-beta 1 and 2 at temperatures as high as 65 degree but loss it activity upon heating at 100 degree.

FIGS. 13A and 13B show TGF-β isoforms Compete for Binding to NC1. As shown in FIG. 13A, we mixed recombinant NC1 with each TGF beta isoform and then performed immuno-precipitation with an anti-NC1 antibody. We then ran the precipitate out on a SDS-PAGE gel and performed a immunoblot using antibodies to each TGF beta isoform. Please note that in accordance with the antigen-to-antigen ELISA data, by immunoprecipitation, NC1 binds to all three TGF-beta isoform. In the lower panel experiment, we examined if NC1 utilizes the same binding site for all three TGF beta isoform by an antigen-to-antigen ELISA competition assay. Please note that binding of NC1 to TGF beta 1 was inhibited by 50% and by 90% by presence of 10-fold excesses of TGF-beta 2 and beta 3, respectively. These data indicate that the 3 TGF beta isoforms bind to the same site of NC1.

FIGS. 14A and 14B show that RDEB patients have severe scarring, contractures and mitten deformities. FIGS. 14A and 14B the severe scarring and fibrotic mitten deformities that are characteristic of patients with RDEB. Aggressive and usually fatal skin cancers develop in areas of scarring and chronic wounds that frequently took the patients' life. These children have a gene defect in the COLA1 gene leading to abnormal type VII collagen, the major component of anchoring fibrils. FIG. 14C is an electron micrograph of normal human skin, showing that these are large structures located that the dermal-epidermal junction and function to hold the epidermis and dermis together. The electron micrograph of FIG. 14D is RDEB skin showing a paucity of anchoring fibrils and clear epidermal-dermal separation.

FIGS. 16A and 16B show an in vitro collagen lattice contraction assay to compare the contraction activity of fibroblasts derived from 6 RDEB patients (PT1 to PT) with fibroblasts from normal human subjects in the presence and absence of growth factors (GF). Note that RDEB fibroblasts exhibited enhanced contraction activity in comparison with normal fibroblasts. RDEB fibroblasts exhibited hypercontraction activity even in the absence of growth factors. These data demonstrate that isolated RDEB fibroblasts retain in culture the ability to contract collagen lattices greater than normal fibroblasts.

FIGS. 17A and 17B shows that the presence of recombinant type VII collagen could inhibit the hyper-contractability of collagen lattices of RDEB fibroblasts in RDEB patients. As shown in FIG. 17B, the addition of recombinant C7 to the collagen lattice contraction assays inhibited not only growth factor induced but also basal contraction of RDEB fibroblasts.

DETAILED DESCRIPTION OF THE INVENTION

Figure 1:
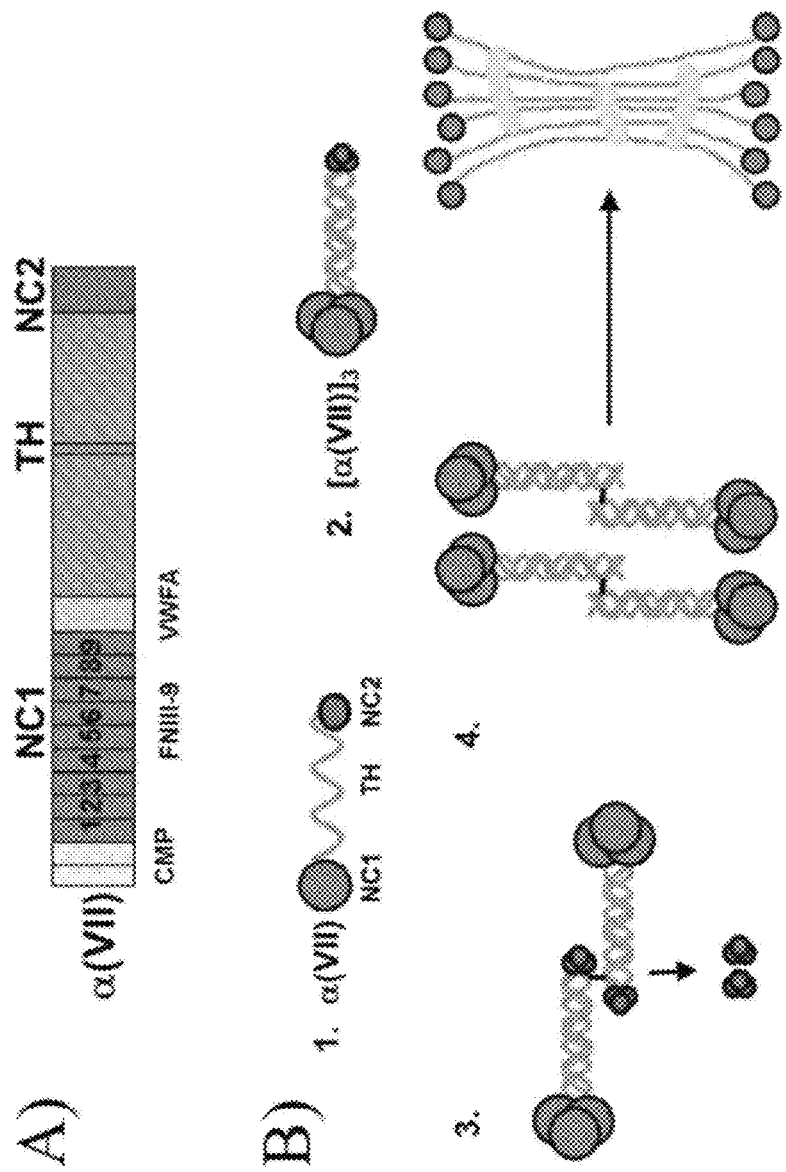
FIG. 1 shows a schematic representation of the domain organization of the proα1 (VII) chain and assembly of the Collagen 7 molecules into anchoring fibrils. Type VII collagen consists of three identical alpha chains, which form a homotrimer. Two C7 molecules align at their carboxy ends to form anti-parallel dimers, which then laterally aggregate to form anchoring fibrils.

Certain terms are first defined. Additional terms are defined throughout the specification.

"Chronic administration", as used herein, refers to the administration of more than one dose of an agent over a period of time. Chronic administration can include regular administration for an extended period of time. Chronic administration can also include the administration of therapy over a prolonged period of time (in some cases, for the duration of a subject's lifetime) so that the concentration of the therapeutic agent is maintained at a therapeutically or prophylactically effective level throughout the course of treatment.

An "effective amount" of Collagen 7 or functional fragment or variant thereof refers to the amount of Collagen 7 or functional fragment or variant thereof, when administered in an accumulate of multiple doses, or as part of any other type of defined treatment regimen, produces a measureable statistical improvement in outcome, as evidenced by at least one clinical parameter associated with the complication.

"Recombinant", as used herein, in reference to a protein or polypeptide molecule, pertains to a protein or polypeptide molecule expressed utilizing isolated nucleic acid molecules or recombinant nucleic acid molecules.

An "isolated" protein refers to a protein that is removed from at least 90% of at least one component of a natural sample from which the isolated protein can be obtained. Proteins can be "of at least" a certain degree of purity if the species or population of species of interest is at least 5, 10, 25, 50, 75, 80, 90, 92, 95, 98, or 99% pure on a weight-weight basis.

The terms "protein" and "polypeptide" as used interchangeably herein.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment." In the present disclosure, one or more symptom of scarring can be prevented. For example, scarring in subjects with EB (e.g., DEB, e.g., RDEB or DDEB) can result in one or more of the following symptoms: contractures, e.g., flexion contractures (e.g., of the extremities); pseudosyndactyly, e.g., pseudosyndactyly of the hands and pseudosyndactyly of the feet; carcinoma (e.g., squamous cell carcinoma); rectal lesions; mucosal lesions; bulla formation; bulla formation post manual trauma; nail deformities; teeth deformities; constricted esophagus; eye disorders, anemia, malnutrition; secondary skin infection; sepsis; hoarse voice; urethral stenosis; phimosis; corneal scarring; malabsorption; and failure to thrive.

"Treating" a subject refers to subjecting the subject to a pharmaceutical treatment, e.g., the administration of a drug, such that at least one symptom of the disease is cured, alleviated or decreased.

A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition are outweighed by the therapeutically beneficial effects.

A "patient", "subject" or "host" (these terms are used interchangeably) to be treated by the subject method may mean either a human or non-human animal.

Any of the treatments described herein can be administered in combination with another agent or therapy. The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order. In some embodiments, the delivery of one agent or therapy is still occurring when the delivery of the second begins, so that there is overlap in terms of administration. This is sometimes referred to herein as "simultaneous" or "concurrent delivery". In other embodiments, the delivery of one agent or therapy ends before the delivery of the other begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Collagen 7 and Variants Thereof

One aspect of the present invention is directed to pharmaceutical compositions comprising collagen 7 and/or a variant thereof and treatment methods based on the administration of collagen type 7 and/or a variant thereof. These methods, as described herein, include methods for accelerating wound closure, or inhibiting or reducing fibrosis or scarring by administering an effective amount of a pharmaceutical composition comprising collagen 7 and/or a variant thereof.

"Collagen 7" as used herein refers to collagen type 7 encoded by the COL7A1 gene. Collagen 7 consists of 2,944 amino acids (SEQ ID NO:1). It comprises a non-collagenous NC1 domain (including residues 17-1253 of SEQ ID NO:1), the central collagenous helical domain (residues 1254-2783 of SEQ ID NO:1), and the carboxyl-terminal NC2 domain (residues 2784-2944 of SEQ ID NO:1).

Variants of Collagen 7 include polypeptides that have substantial identity with the functional fragment of Collagen 7 that maintains the ability to form anchoring fibrils between the epidermal and dermal layers of human skin. Collagen 7 variants include, but are not limited to, Collagen 7 polypeptides that have been either chemically modified relative to Collagen 7 and/or contain one or more amino acid sequence alterations relative to Collagen 7.

Variants of Collagen 7 include polypeptides having at least 75%, 80%, 85%, 90%, 95%, 96%, 97%, 98% or 99% identity with the amino acid sequence of human Collagen 7 (see infra). Calculations of "identity" or "sequence homology" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Variants of Collagen 7 also include polypeptides having amino acid modifications (e.g., deletions, additions or substitutions, such as conservative substations) from the amino acid sequence of Collagen 7 (See infra). For example, a variant of Collagen 7 can differ by at least 1, 2, 3, 4, 5 but not more than 50, 40, 30, 20, 15 or 10 amino acids from Collagen 7 (see infra). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Polypeptides: Functional Fragments of Collagen 7 and Variants Thereof

One aspect of the present invention is directed to functional fragments of Collagen 7 and variants thereof, preferably isolated functional fragments and variants thereof and pharmaceutical compositions, and treatments based thereon. As used herein, a functional fragment of Collagen 7 refers to a portion of Collagen 7 that maintains the ability to bind to TGF-β1 and inhibit profibrogenic TGF-β1 and TGF-β2 activity but does not include the entirety of Collagen 7's 2,944 amino acid residues. Optionally, the functional fragment may be sized and constructed so that it does not maintain an ability to form anchoring fibrils between the epidermal and epidermal layers of human skin but nonetheless maintains the ability to bind to TGF-β1 and inhibit profibrogenic TGF-β1 and TGF-β2 activity.

A functional fragment of the present invention may be formulated as pharmaceutical composition and used in connection with treatment methods based on the administration of the selected functional fragment and/or a variant thereof. These methods, as described herein, include methods for accelerating wound closure, or inhibiting or reducing fibrosis and/or scarring by administering an effective amount of a pharmaceutical composition comprising the selected functional fragment and/or a variant thereof.

A functional fragment of the present invention generally comprises at least one of the nine fibronectin type III-like repeats ("FNIII") of Collagen 7's NC1 region, which are:

Fibronectin Type III Region 1 (residues 233 to 325 of SEQ ID NO:1) ("FNIII Region 1")

Fibronectin Type III Region 2 (residues 333 to 413 of SEQ ID NO:1) ("FNIII Region 2")

Fibronectin Type III Region 3 (residues 419 to 492 of SEQ ID NO:1) ("FNIII Region 3")

Fibronectin Type III Region 4 (residues 509 to 587 of SEQ ID NO:1) ("FNIII Region 4")

Fibronectin Type III Region 5 (residues 598 to 680 of SEQ ID NO:1) ("FNIII Region 5")

Fibronectin Type III Region 6 (residues 687 to 771 of SEQ ID NO:1) ("FNIII Region 6")

Fibronectin Type III Region 7 (residues 777 to 862 of SEQ ID NO:1) ("FNIII Region 7")

Fibronectin Type III Region 8 (residues 867 to 952 of SEQ ID NO:1) ("FNIII Region 8") and Fibronectin Type III Region 9 (residues 955 to 1044 of SEQ ID NO:1) ("FNIII Region 9").

In one embodiment, the functional fragment includes all of the NC1 domain of Collagen 7, i.e. it includes the entire non-collagenous NC1 domain (i.e., residues 17-1253 of SEQ ID NO:1). In one embodiment, this functional fragment does not include the central collagenous helical domain, e.g., amino acid residues 1920-2603 of SEQ ID NO:1 the central collagenous helical domain of Collagen 7 and/or the carboxyl-terminal NC2 domain (residues 2784-2944 of SEQ ID NO:1). Alternatively, the functional fragment may include a fragment of less than 100, 50, 40, 20 or 10 amino acid residues of the central collagenous helical domain and/or less than 40, 20 or 10 amino acid residues of the carboxy terminal NC2 domain.

One embodiment of the present invention is thus an isolated polypeptide comprising an amino acid sequence corresponding the entire NC1 region or variants thereof.

In a preferred embodiment, the functional fragment is a polypeptide that includes at least one of FNIII Region 1, FNIII Region 5 and FNIII Region 6.

Thus, one embodiment of the present invention is an isolated polypeptide comprising an amino acid sequence corresponding to FNIII Region 1 or a variant thereof. In one embodiment, the isolated polypeptide may further comprise an amino acid sequence corresponding to FNIII Region 5 and/or FNIII Region 6 or a variant thereof. In another embodiment, this polypeptide does not include an amino acid sequence corresponding to any other FNIII Region not specifically included in the polypeptide sequence, any other NC1 region or the collagenous or NC2 domains of Collagen 7 or any combination of these.

Another embodiment of the present invention is an isolated polypeptide comprising an amino acid sequence corresponding to FNIII Region 5 or a variant thereof. In one embodiment, the isolated polypeptide may further comprise an amino acid sequence corresponding to FNIII Region 1 and/or FNIII Region 6 or a variant thereof. In another embodiment, this polypeptide does not include an amino acid sequence corresponding to any other FNIII Region not specifically included in the polypeptide sequence, or any other NC1 region or the collagenous or NC2 domains of Collagen 7, or any of combination of these.

Another embodiment of the present invention is an isolated polypeptide comprising an amino acid sequence corresponding to FNIII Region 6 or a variant thereof. In another embodiment, this polypeptide does not include an amino acid sequence corresponding to any other FNIII Region not specifically included in the polypeptide sequence, any other NC1 region or the collagenous or NC2 domains of Collagen 7 or any combination of these.

Another embodiment of the present invention is an isolated polypeptide comprising an amino acid sequence corresponding to PCR1 or a variant thereof.

Another embodiment of the present invention is an isolated polypeptide comprising an amino acid sequence corresponding to PCR2 or a variant thereof.

Another embodiment of the present invention is an isolated polypeptide comprising an amino acid sequence corresponding to PCR3 or a variant thereof.

Another embodiment of the present invention is an isolated polypeptide comprising an amino acid sequence corresponding to PpuMI or a variant thereof.

Another embodiment of the present invention is an isolated polypeptide comprising an amino acid sequence corresponding to FP15 or a variant thereof.

Another embodiment of the present invention is an isolated polypeptide comprising an amino acid sequence corresponding to FP16 or a variant thereof.

A variant of a functional fragment of Collagen 7 refers to a polypeptide that has substantial identity with the functional fragment of Collagen 7 and that maintains the ability of the functional fragment to bind to TGF-β1 and inhibit profibrogenic TGF-β1 and TGF-β2 activity. Functional fragment variants include, but are not limited to, polypeptides that have been either chemically modified relative to the functional fragment and/or contain one or more amino acid sequence alterations relative to Collagen 7.

Variants of a functional fragment of Collagen 7 include polypeptides having at least 75%, 80%, 85%, 90%, 95%, 96%, 97%, 98% or 99% identity with the amino acid sequence of the functional fragment. Calculations of "identity" or "sequence homology" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Variants of a functional fragment of Collagen 7 also include polypeptides having amino acid modifications (e.g., deletions, additions or substitutions, such as conservative substations) from the amino acid sequence of Collagen 7 (See infra). For example, a variant of a functional fragment can differ by at least 1, 2, 3, 4, 5 but not more than 10 amino acids from Collagen 7 (see infra). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Indications and Treatment Methods

Treatment methods involving the administration collagen 7, a functional fragment, and a variant according to the present invention may generally be employed when it is clinically desirable to either (i) accelerate wound closure, or (ii) prevent, inhibit or reduce scarring or fibrosis. Accelerated would closure, reduced scarring and reduced fibrosis may be measured relative to untreated controls. While not being limited to theory, it is believed that these effects are achieved, at least in part, via binding to and decreasing pro-fibrogenic TGF-β activities. Fibrosis can be defined as the replacement of the normal structural elements of the tissue by distorted, non-functional or excessive accumulation of scar tissue. Scar tissue is perhaps the most significant biological marker for fibrosis.

One embodiment of the present invention is directed to a pharmaceutical composition comprising Collagen 7, or a functional fragment or variant thereof, and one or more pharmaceutically acceptable carriers, for use in treating a subject at risk for developing scarring or fibrosis or used in connection with treatment for existing scars or fibrosis. The disclosure features a pharmaceutical composition comprising Collagen 7, or a functional fragment or variant thereof, as described herein, and one or more pharmaceutically acceptable carriers for use in preventing scarring or fibrosis, or reducing the extent of degree of fibrosis or scarring. Treatment methods according to this embodiment comprises administering to a patient in need thereof an effective amount of C7 and/or a functional fragment or variant thereof.

In one embodiment, the subject to be treated is a person having dystrophic epidermolysis bullosa (EB), which is caused by mutations in the COL7A1 gene, the gene which encodes for the protein Collagen 7. Epidermolysis bullosa is a group of inherited genetic conditions that cause the skin to be very fragile and to blister easily. EB (e.g., DEB, e.g., RDEB or DDEB) symptoms associated with scarring include, but are not limited to, contractures, e.g., flexion contractures (e.g., of the extremities); pseudosyndactyly, e.g., pseudosyndactyly of the hands and pseudosyndactyly of the feet; carcinoma (e.g., squamous cell carcinoma); rectal and anal lesions; urethral lesions; mucosal lesions; lesions of squamous epithelial tissue; lesions of the gastrointestinal tract; bulla formation; bulla formation post manual trauma; nail deformities; teeth deformities; constricted esophagus; eye disorders, anemia, malnutrition; secondary skin infection; sepsis; hoarse voice; urethral stenosis; phimosis; corneal scarring; malabsorption; and failure to thrive. In a patient with EB, an effective amount of Collagen 7 or a functional fragment or variant thereof is generally administered to a patient having at least one EB symptom associated with scarring.

Patients with dystrophic epidermolysis bullosa (DEB) have incurable skin fragility, blistering and multiple skin wounds that result in extensive scar formation, contractures and mitten deformities. It is caused by mutations in the gene that encodes for type VII collagen (C7). We showed previously that topical application of recombinant C7 to murine skin wounds decreased the expression of fibrogenic transforming growth factor β2 (TGF-β2) and increased the expression of anti-fibrogenic TGF-β3, accompanied by the reduced expression of several fibrosis markers, such as connective tissue growth factor (CTGF) and α-SMA-positive myofibroblasts. In this study, we used skin samples and primary cultures of fibroblasts and keratinocytes derived from ten RDEB patients or normal human subjects to compare the expression of TGF-β isoforms and various genes involved in TGF-β induced fibrosis signaling pathways. Immunostaining of skin samples from RDEB patients revealed the increased expression of pro-fibrogenic TGF isoforms (TGF-β1 and TGF-β2), canonical TGF-β1 signaling (phospho-Smad2/3, CTGF), non-canonical TGF-β1 signaling (p-AKT), and extracellular matrices (collagen 1, tenascin and fibronectin). Immunoblotting analysis of cellular extracts showed the upregulation of TGF-β1, TGF-β2, TGF-β receptor 1, p-Smad2/3, CTGF, p-AKT in RDEB keratinocytes and p-AKT, periostin, Slug and collagen I in RDEB fibroblasts. Re-expression of wild type COL7A1 in RDEB fibroblasts or keratinocytes via lentiviral vectors or supplementing RDEB cells with recombinant C7 decreased the expression of TGF-β1, TGF-β2, TGF-β receptor 1, p-Smad2/3, CTGF, p-AKT, periostin, Slug and collagen 1. In addition, reduction of COL7A1 via siRNA in normal dermal fibroblasts and keratinocytes led to increased expression of TGF-β1, p-AKT, and Slug. These results indicate that loss of C7 in RDEB patients upregulates profibrotic TGF-β signaling and induces a distinct profibrotic gene expression program, suggesting that local application of C7 may have a therapeutic effect in controlling fibrosis seen in RDEB patients. (or our data provide new insight into the molecular mechanisms that may underpin the development of fibrosis and scar in RDEB patients.)

In another embodiment of the present invention, the subject to be treated is a person having no mutation in the COL7A1 gene. Numerous clinical indications are associated with scarring and fibrosis in the non-EB population, including keloids and hypertrophic scars in the skin, tendon adhesions, transmission blockage following nerve injury, scleroderma, Crohn's disease, esophageal strictures, urethral strictures, capsules around breast implants, liver cirrhosis, atherosclerosis and fibrotic non-union in bone. Hypertrophic scars or keloids may form, for instance, as a result of injury, including burns, surgery and acne. It should be noted that a person with EB may be at risk for fibrosis or scarring resulting from these same clinical indications and can likewise benefit from treatments according to the present invention even when treatment with collagen 7 is not indicated as a separate treatment for EB.

Subject Selection

Subjects who may benefit from the use of the methods described herein include, but are not limited to, subjects who have or at risk for developing scarring or fibrosis.

Preparation of Collagen 7 and Functional Fragments and Variants Thereof

Collagen 7 and functional fragments and variants thereof can be synthesized by standard molecular biology techniques in standard cell lines, e.g., CHO, HEK293, fibroblast or keratinocyte cells. Standard cell culture procedures and conditions may be used for culture of host cells described herein and are known to those skilled in the art. Host cells cultured for expression of recombinant Collagen 7, such as HEK293 cells, may be cultured in routinely used cell culture media (e.g. Dulbecco's modified Eagle's medium (DMEM)/ Ham's F-12 (1:1) with suitable supplementation of serum, antibiotics, etc, dependent on the application) as referenced in, ((Chen et al. *J Bio Chem* 277(18): 2118-2124 (2002)), (Chen et al. *J Bio Chem* 275: 32(11): 24429-24435 (2000)), (Chen et al. *J Bio Chem* 276(24): 21649-21655 (2001)).

Host cells may be engineered to express other proteins to optimize production of the recombinant Collagen 7. This may include, but not limited to, the co-expression of the processing enzymes prolyl hydroxylase, prolidase, or glycosyl-transferase, by exogenously introducing isolated nucleic acid or recombinant expression vectors encoding the appropriate nucleic acid sequence, in host cells comprising Collagen 7 nucleic acid sequence or recombinant expression vector. The triple helical assembly of Collagen 7 often requires hydroxylation and the presence of ascorbic acid in the host cell growth media. As demonstrated in the reference, (Chen et al. *J Bio Chem* 277 (18): 2118-2124 (2002)), recombinant type 7 collagen produced, recovered, and purified from HEK293 cells in the presence of ascorbic acid was secreted as an approximately 900-kDa protein, corresponding to the association of three type 7 collagen monomers (each monomer 290-kDa). Ascorbic acid may be used in the host cell culture conditions to aid in proper processing and assemblying of the recombinant protein.

Suitable vectors for use herein are those that can express Collagen 7, prolyl hydroxylase, prolidase, or glycosyl-transferase, or a functional portion thereof. In order to express the proteins described herein, the nucleotide sequence encoding the appropriate protein, or a functional equivalent, can be inserted into a suitable vector. A suitable vector contains the necessary and appropriate transcriptional and translational control sequences for expression of the inserted nucleic acid sequence. Standard methods, known to those skilled in the art, may be used to construct the recombinant expression vectors containing the nucleic acid sequences described herein. These methods include, but are not limited to, in vitro recombinant techniques, synthetic techniques, and in vivo recombination/genetic recombination; the choice of method depends on the nature of the specific nucleotide fragments and may be determined by persons skilled in the art.

Suitable vectors for use herein may contain an origin of replication and a restriction endonuclease sequence site. Persons skilled in the art would have knowledge of suitable origin of replication and restriction endonuclease sequences for use in the host cell. Suitable vectors for use herein may contain sequence elements to aid transcription, including, but not limited to, promoter and enhancer elements. Persons skilled in the art would have knowledge of various transcriptional control elements, including but not limited to, promoters, inducible promoters, and enhancer elements, that would be suitable in the host cell. Suitable vectors for use herein may also contain a selectable marker gene that encodes a product necessary for the host cell to grow and survive under specific conditions, aiding in the selection of host cells into which the vector has been introduced. Typical selection genes may include, but are not limited to, genes encoding a protein that confers resistance to an antibiotic, drug, or toxin (e.g., tetracycline, ampicilin, neomycin, hygromycin, etc). Persons skilled in the art would have knowledge of coding sequences for suitable selectable markers and reporter genes for use in the host cell.

Expression vectors described herein can be introduced into host cells via conventional transformation or transfection techniques. Transformation and transfection techniques include, but are not limited to, calcium phosphate or calcium chloride coprecipitation, DEAE-dextran-mediated transfection, lipofectamine, electroporation, microinjection, and viral mediated transfection (as referenced in U.S. Pat. No. 6,632,637 (McGrew)). Persons skilled in the art would have knowledge of suitable transformation and transfection methods based on the host cell/vector combination. For long term, high yield production of recombinant proteins, stable expression of the recombinant protein may be preferred. Host cells that stably express the recombinant protein may be engineered.

The recombinant expression vectors described herein may be introduced into a suitable host cell, which may include a living cell capable of expressing the protein coding region from the defined recombinant expression vector. The term "host cell" refers not only to the particular subject cell but to the progeny or potential progeny of the particular subject cell. Because certain modifications may occur in succeeding generations due to either mutation or environmental influences, such progeny may not in fact, be identical to the parent cell, but are still included within the scope of the term as used herein. Various host cell expression systems may be utilized to express the nucleic acid molecules described herein. These include, but are not limited to yeast or fungi, transformed with recombinant yeast or fungi expression vectors containing the appropriate nucleic acid sequence; insect cell systems infected with recombinant virus expression vectors or transformed with recombinant plasmid expression vectors containing the appropriate nucleic acid sequence; or mammalian cell systems (e.g., primate cell, human cell, rodent cell, etc) transfected with expression vectors containing the appropriate nucleic acid sequence. Suitable host cells may include primary or transformed cell lines, including, but not limited to, fibroblasts, CHO, HEK293, C127, VERO, BHK, HeLa, COS, MDCK, etc (as referenced in U.S. Pat. No. 6,632,637 (McGrew)). Other suitable host cells are known to those skilled in the art.

Modifications, including, but not limited to, glycosylation, phosphyorylation, hydroxylation, and processing of protein products may be important to the function of a protein. Different host cells have various characteristics and mechanisms for post-translational processing and modification of proteins. A host cell that is capable of modulating expression of the nucleic acid sequences contained in the vector, or modulating expression of the vector nucleic acid sequences, or modifying and processing the gene product encoded in the vector sequence in a specific manner may be chosen. Mammalian host cells may be chosen to ensure the correct modification and processing of the recombinant protein. Such mammalian host cells may include, but are not limited to, CHO, HEK293, human fibroblasts, and human keratinocytes.

Proteins produced by recombinant methods described herein may be recovered from the host cell culture system according to standard protocols known in the art (e.g., precipitation, centrifugation, etc). Recombinant Collagen 7 described herein may be secreted into the host cell medium and recovered by ammonium sulfate precipitation and subsequent centrifugation; as demonstrated in the following reference, (Chen et al. *J Bio Chem* 277(18): 2118-2124 (2002)). Proteins produced and recovered by recombinant and molecular biology methods described herein, may be purified according to standard protocols known in the art (e.g., dialysis, stepwise salt solubilization, ion exchange chromatography, affinity chromatography, SDS gel electrophoresis, etc). The recombinant Collagen 7 described herein may be purified to homogeneity by ion exchange chromatography; as demonstrated in the following reference, (Chen et al. *J Bio Chem* 277(18): 2118-2124 (2002)).

Optionally Collagen 7 or its functional fragments may be further purified. Purification may be achieved using any method known in the art, including, but not limited to affinity chromatography, e.g., an anti-Collagen 7 antibody column; hydrophobic interaction chromatography; ion exchange chromatography; size exclusion chromatography; electrophoretic procedures, e.g., isoelectric focusing, differential solubility (e.g., ammonium sulfate precipitation), or extraction, and the like.

Pharmaceutical Compositions

The disclosure provides a pharmaceutical composition comprising Collagen 7 or a functional fragment or variant thereof. Pharmaceutical compositions may take the form of any acceptable pharmaceutical formulation. Pharmaceutical compositions can be formulated in a variety of different forms, such as liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application.

Exemplary pharmaceutical compositions are described below. The pharmaceutical compositions include those suitable for parenteral (including intravenous, subcutaneous, intradermal, intramuscular, and intraarticular), topical (including dermal, transdermal, transmucosal, buccal, sublingual, and intraocular), and rectal administration, although the most suitable route may depend upon, for example, the condition and disorder of the recipient.

Compositions for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The composition may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as EDTA, mannitol, 1,3-butanediol, water, Ringer's solution, an isotonic sodium chloride solution, or other suitable dispersing or wetting and suspending agents. The compositions may contain pharmaceutically acceptable substances or adjuvants, including, but not limited to, EDTA, e.g., 0.5 mM EDTA; pH adjusting and buffering agents and/or tonicity adjusting agents, e.g., sodium acetate, sodium lactate, sodium chloride, potassium chloride, calcium chloride, sorbitan monolaurate; minor amounts of non-toxic auxiliary substances, such as wetting or emulsifying agents or preservatives.

It should be understood that in addition to the ingredients particularly mentioned above, the composition may include other agents conventional in the art having regard to the type of formulation in question.

Chronic Administration Regimen

In practicing the methods described herein, Collagen 7 or a functional fragment or variant thereof may be chronically administered. Chronic administration can include the administration of more than one dose of an agent over a period of time. Chronic administration can include regular administration for an extended period of time, typically over the period of time a person is at risk for scarring or fibrosis.

Combination Treatments

The present disclosure encompasses combined administration of an additional agent or treatment regimen with Collagen 7 or a functional fragment or variant thereof. The additional agent may include, but is not limited to, antibiotics, analgesics, opioids, anti-virals, anti-inflammatory agents, or nutritional supplements.

In one embodiment, the additional agent or treatment regimen may be an agent or treatment regimen designed to treat an underlying disease or condition that places the subject at risk for scarring or fibrosis.

In another embodiment, the additional agent or treatment regimen may be another agent or treatment regimen designed to accelerate or promote healing.

In one embodiment, the additional agent or treatment regimen may be another agent/treatment regimen designed to treat and/or prevent scarring or fibrosis. Such agents or treatment regimens may include, but are not limited to, corticosteroid injections, silicon sheeting, surgery, scar excision, imiquimod, pulsed laser techniques (typically using a 585 nm pulsed dye laser), intralesional verapamil, fluorouracil, bleomycin, and interferon alfa-2b injections.

EXEMPLIFICATION

Example 1: Assembly of Collagen 7 into Anchoring Fibrils

FIG. 1 is a schematic representation of the domain organization of the proα1 (VII) chain and assembly of the Collagen 7 molecules into anchoring fibrils. As shown in FIG. 1(A), the proα1 (VII) polypeptide consists of a collagenous segment (TH) characterized by repeating Gly-X-Y sequences which contain several non-helical segments. The collagenous domain is flanked by a large amino-terminal noncollagenous domain (NC-1) and a short carboxy-terminal noncollagenous domain (NC2). As shown in FIGS. 1(B)(1) and (2), three Collagen 7 alpha chains form a homotrimer. In FIG. 1(B)(3). In the extracellular space, the proα1 (VII)$_3$ chains align into antiparallel dimers as part of the NC-2 is proteolytically removed. As shown in FIG. 1(B)(4), the Collagen 7 antiparallel dimers then laterally assemble to form anchoring fibrils, which can be recognized by the characteristic centrosymmetric banding pattern observed with transmission electron microscopy.

Example 2: Collagen 7 and NC1 Bind to TGF-β1, TGF-β2, and TGF-β3

Figure 2:
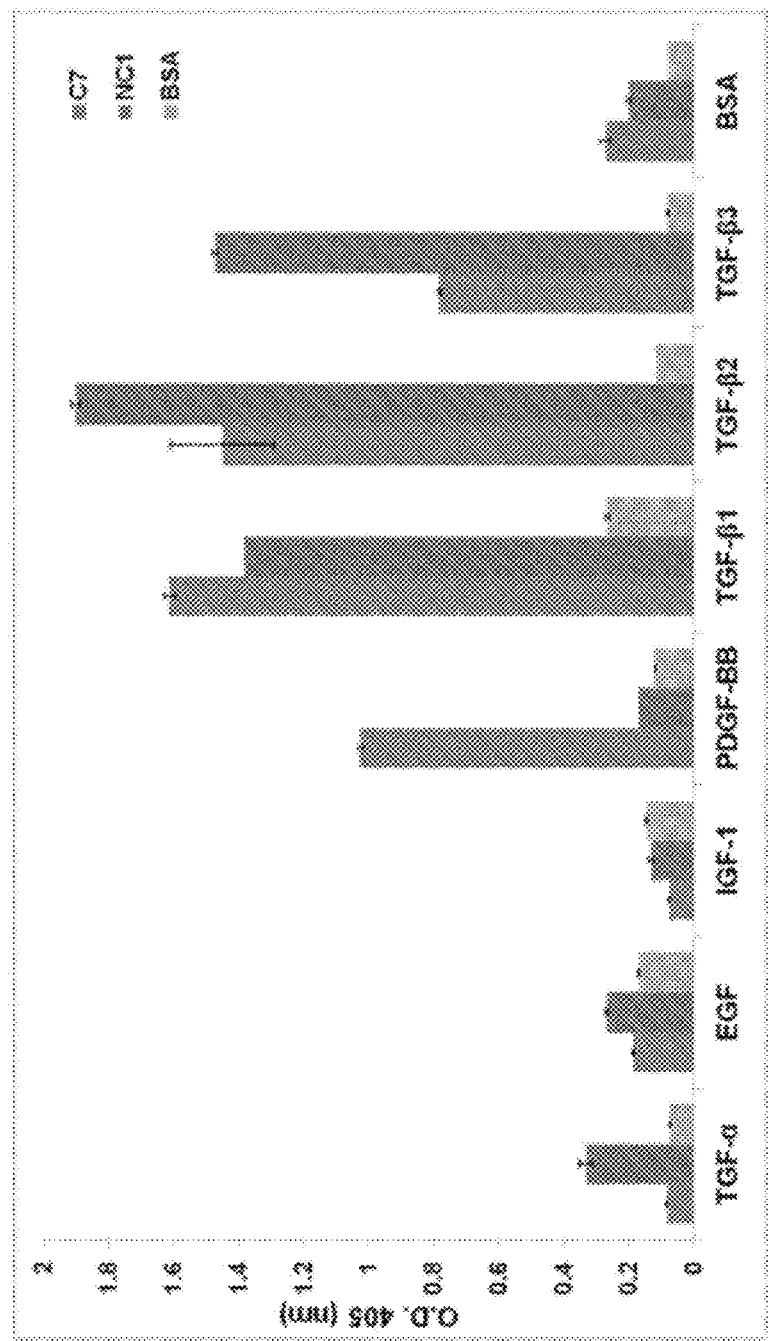
FIG. 2 shows the identification of growth factor binding sites in Collagen 7 and NC1.

FIG. 2 shows the identification of growth factor binding sites in Collagen 7 and NC1. Solid phase ligand binding assay was used to determine the binding of either Collagen 7 of NC1 to transforming growth factors Alpha, Beta 1, Beta 2, and Beta 3 (TGF-α, TGF-β1, TGF-β2, and TGF-β3), Platelet-Derived Growth Factor BB (PDGF-BB), Epidermal Growth Factor (EGF), Insulin-like Growth Factor 1 (IGF-1), and BSA. All growth factors were plated onto an ELISA plate at 1.25 µg/ml. 2 µg of purified recombinant Collagen 7 and NC1 was incubated with each protein for 2 hours in PBST at 20° C. Bindings were detected using rabbit anti-NC1 polyclonal anti-NC1 antibodies (1:1000), followed by an alkaline phosphatase-conjugated secondary antibody (1:300). Note that Collagen 7 and NC1 binds to structurally related TGF-β1, TGF-β2 and TGF-β3. Collagen 7, but not NC1, binds to PDGF-BB, implying the binding site for this growth factor resides in either the TH of NC2 domains.

Example 3: Collagen 7 and NC1 Bind to TGF-β Isoforms in a Dose Dependent Manner

Figure 3:
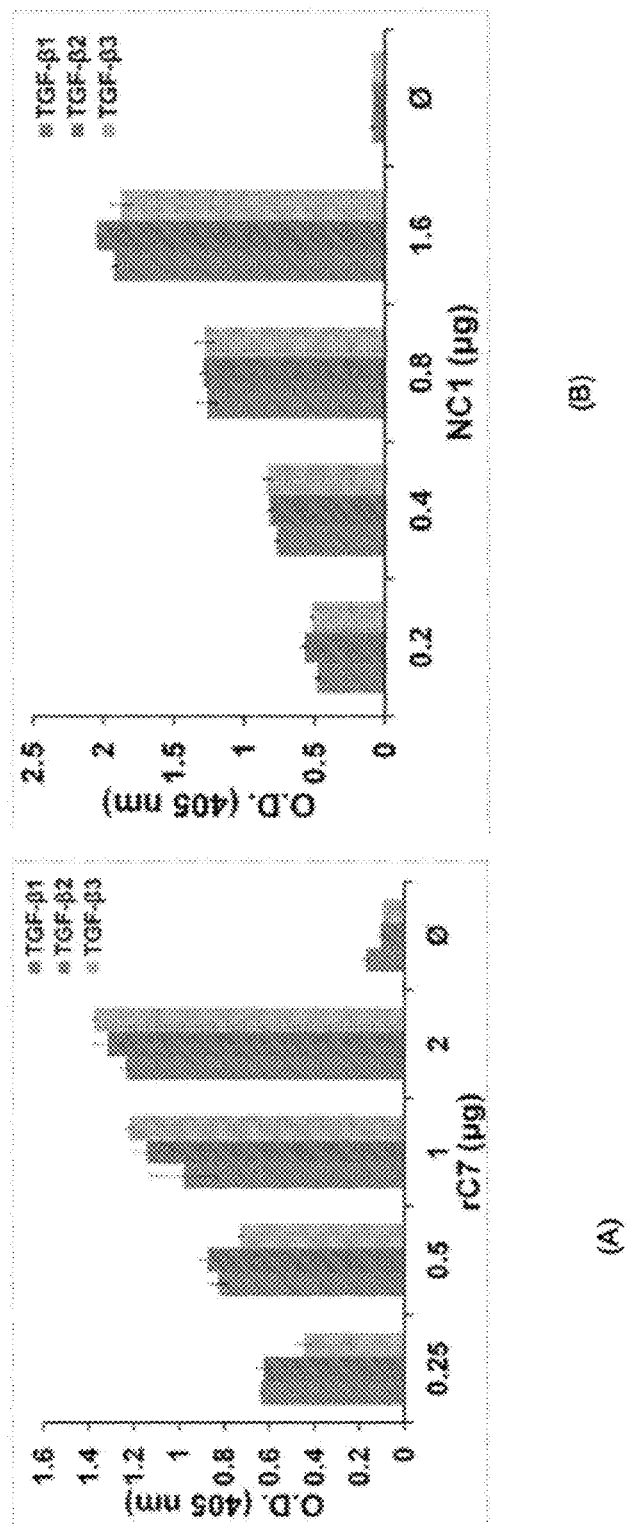
FIG. 3 shows the dose-dependent binding of Collagen 7 and NC1 to all three TGF-β isoforms.

FIG. 3 shows the dose-dependent binding of Collagen 7 and NC1 to all three TGF-β isoforms. ELISA plates were coated with either of the TGF-β isoforms and then incubated with the indicated amounts of either recombinant Collagen 7, NC1 or no protein. Note that there was a dose-dependent interaction between Collagen 7/NC1 and all isoforms of TGF-β. These results indicate that the active region for TGF-β binding is within the NC1 domain of Collagen 7.

Polyclonal anti-NC1 antibody or an antibody to GST, at a dilution of 1:2000 followed by incubation with alkaline phosphatase-conjugated goat anti-rabbit IgG (1:400) (Organon Teknika-Cappel, Durham, N.C.) was used for detection. The development of the colorimetric reaction using p-nitro-phenylphosphate as a substrate (Bio-Rad, Melville, N.Y.) was measured by reading the absorbance of the product at 405 nm (Labsystems Multiskan Multisoft, Finland). A control wavelength was measured at 620 nm.

Example 4: Schematic Representation of Polypeptides Comprising NC1 Subdomains

Figure 4:
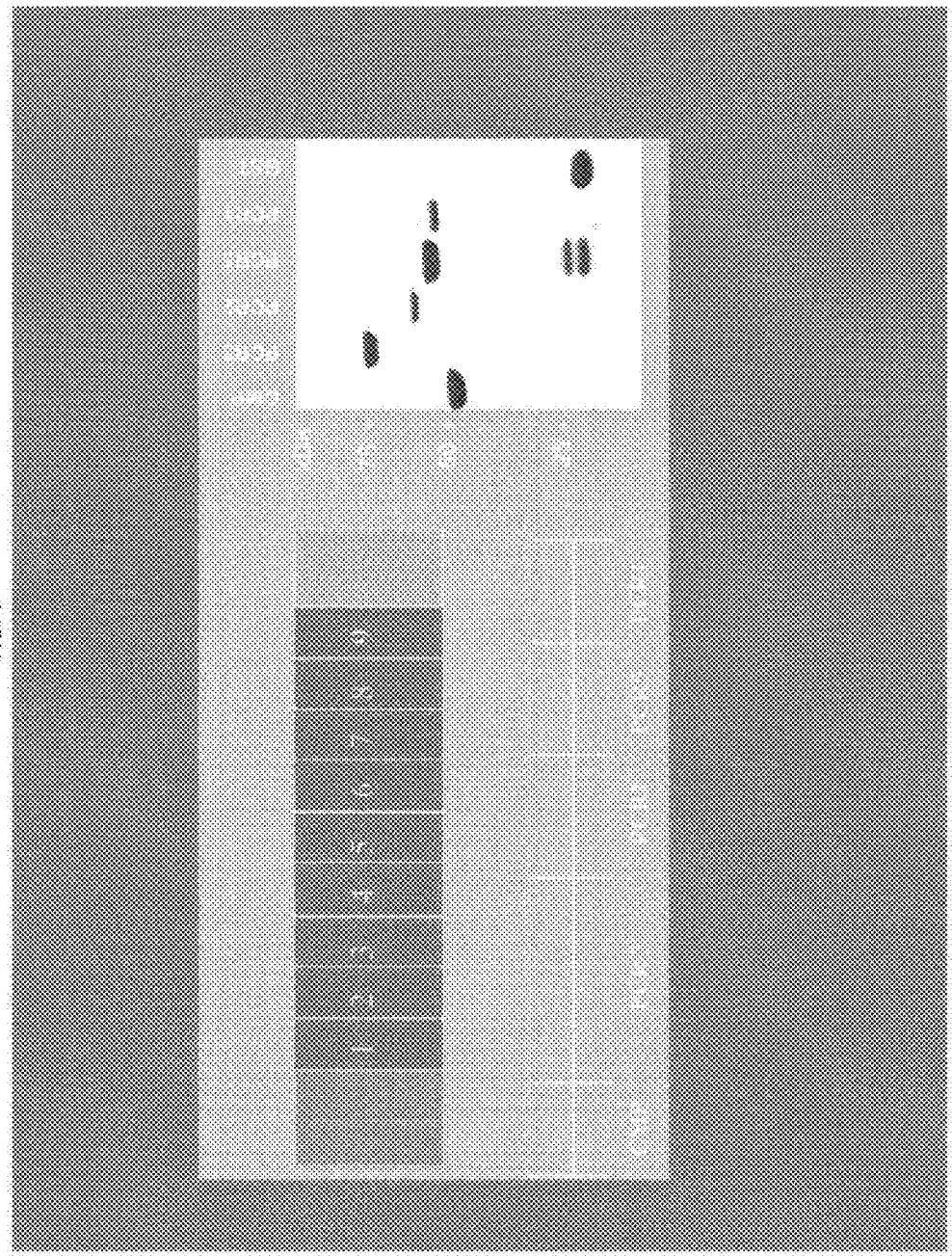
FIG. 4 shows a schematic of bacterial fusion proteins encompassing subdomains of NC1.

FIG. 4 shows a schematic of bacterial fusion proteins encompassing subdomains of NC1. The schematic shows the 5 recombinant fusion proteins encompassing the complete NC1 domain. These GST fusion proteins were expressed from bacteria and purified using a GST affinity column. The picture on the right shows Coomassie Blue staining of these purified proteins resolved by 10% SDS-PAGE.

Example 5: FNIII Subdomains of NC1 Mediate Binding to TGF-β1, TGF-β2, and TGF-β3

Figure 5:
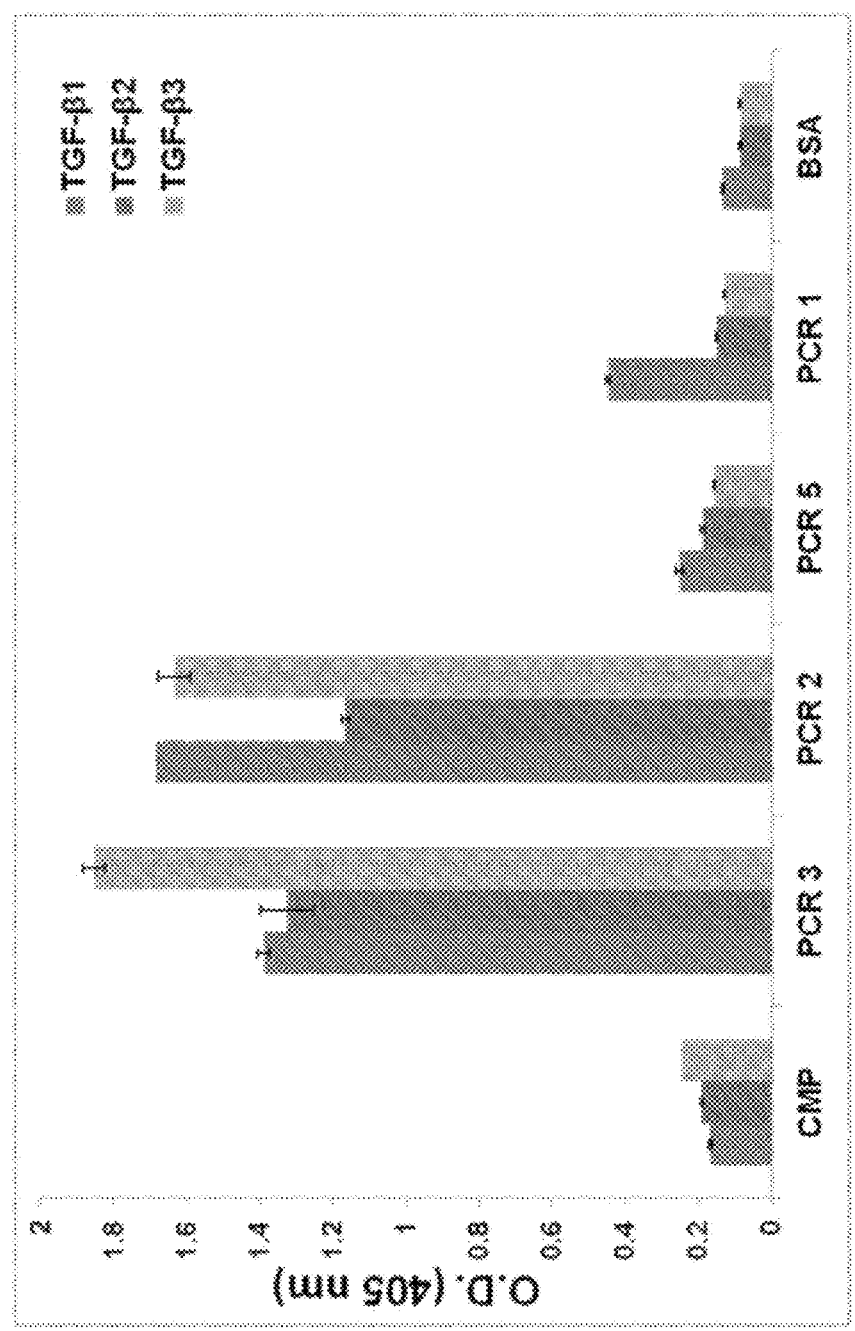
FIG. 5 shows that subdomains of FNIII Mediate Binding of NC1 to TGF-β. Solid phase ligand binding assay was used to determine the binding of recombinant fusion proteins to all three isoforms of TGF-β. TGF-βs 1, 2, and 3 or BSA were plated onto an ELISA plate and incubated with fusion proteins as indicated for 2 hr at room temperature. Binding was detected using an affinity purified polyclonal anti-GST antibody (1:2000), followed by an alkaline phosphate-conjugated secondary antibody (1:300). Note that PCR3 and PCR2 had significant affinity for all three TGF-β isoforms, while all the other fragments showed almost no binding activity.

FIG. 5 shows that Subdomains of FNIII Mediate Binding of NC1 to TGF-β. Solid phase ligand binding assay was used to determine the binding of recombinant fusion proteins to all three isoforms of TGF-β. TGF-βs 1, 2, and 3 or BSA were plated onto an ELISA plate and incubated with fusion proteins as indicated for 2 hr at room temperature. Binding was detected using an affinity purified polyclonal anti-GST antibody (1:2000), followed by an alkaline phosphate-conjugated secondary antibody (1:300). Note that PCR3 and PCR2 had significant affinity for all three TGF-β isoforms, while all the other fragments showed almost no binding activity.

Example 6: NC1 Subdomains Bind to TGF-β in a Dose-Dependent Manner

FIG. 6 shows the dose-dependent binding of NC1 subdomains to all three TGF-β isoforms. ELISA plates were coated with either of the TGF-β isoforms and then incubated with the indicated amounts of either PCR3, PCR2 or no protein. Note that there was a dose-dependent interaction between both NC1 fragments and all isoforms of TGF-β. These results indicate that there are two binding sites for all forms of TGF-β and that the active region for TGF-β binding is within PCR3 and PCR2 subdomains of NC1.

Figure 7:
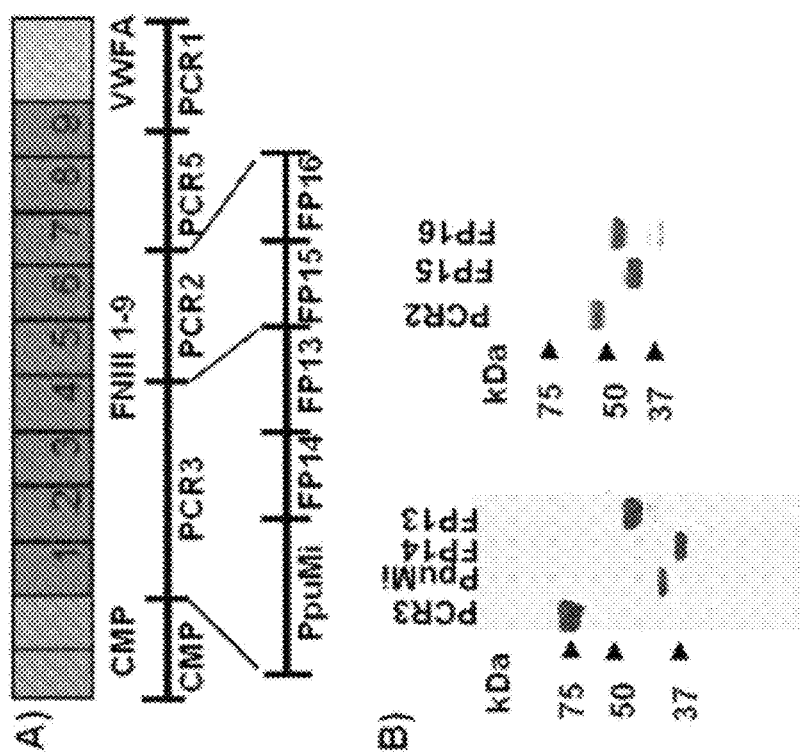
FIG. 7 is a schematic of bacterial fusion proteins within PCR3 and PCR2.

Example 7: PCR 2 and PC3 NC1 Subdomains Bind to TGF-β in a Dose-Dependent Manner FIG. 7 is a schematic of bacterial fusion proteins within PCR3 and PCR2. The schematic of FIG. 7 shows the 5 fusion proteins within both the PCR3 and PCR2. These fusion proteins were expressed from bacteria and purified using a GST affinity column. The picture on the right shows Coomassie Blue staining of these purified proteins resolved by 10% SDS-PAGE.

Example 8: FNIII Subdomains of NC1 Mediate Binding to TGF-β Isoforms

Figure 8:
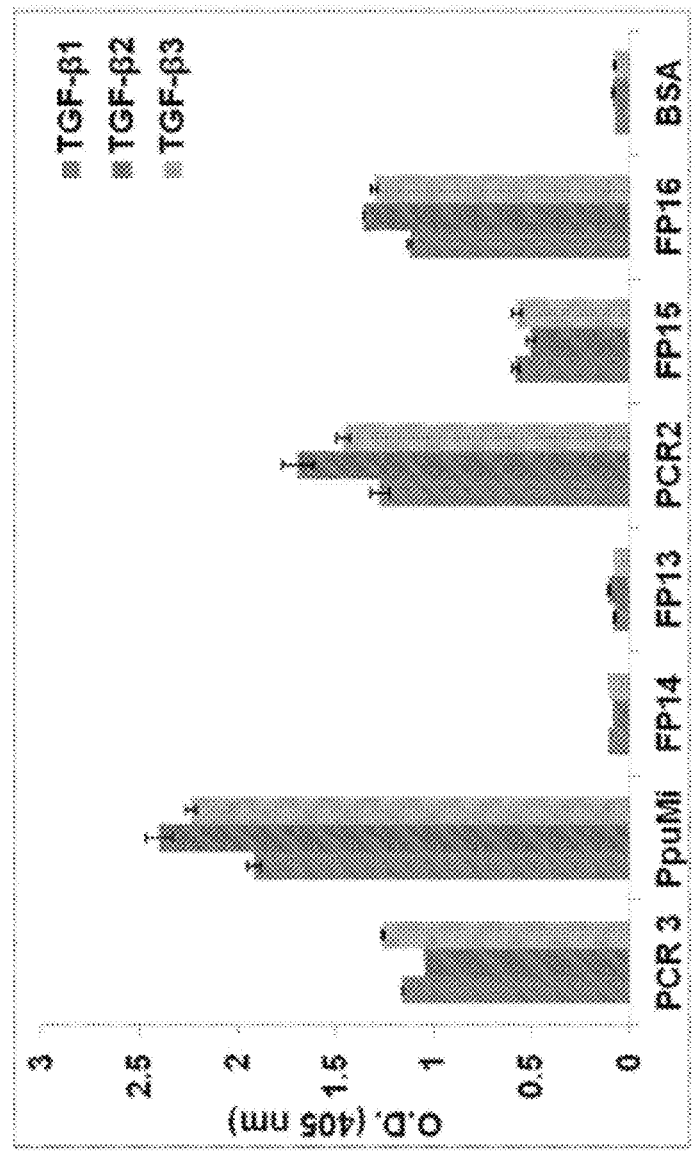
FIG. 8 shows that subdomains of FNIII mediate binding of NC1 to TGF-β.

FIG. 8 shows that subdomains of FNIII mediate binding of NC1 to TGF-β. In FIG. 8, a solid phase ligand binding assay was used to determine the binding of recombinant fusion proteins to all three isoforms of TGF-β. TGF-βs 1, 2, and 3 or BSA were plated onto an ELISA plate and incubated with fusion proteins for 2 hr at room temperature. Binding was detected using an affinity purified polyclonal anti-GST antibody (1:2000), followed by an alkaline phosphate-conjugated secondary antibody (1:300). Note that PpuMi, FP15 and FP16 fragments recapitulate (or even exhibit enhanced) binding to TGF-β isoforms compared to their parent domains. All the other fragments showed almost no binding activity compared to BSA control.

Example 9: PpuMi, FP15 and FP16 Subdomains

Figure 9:
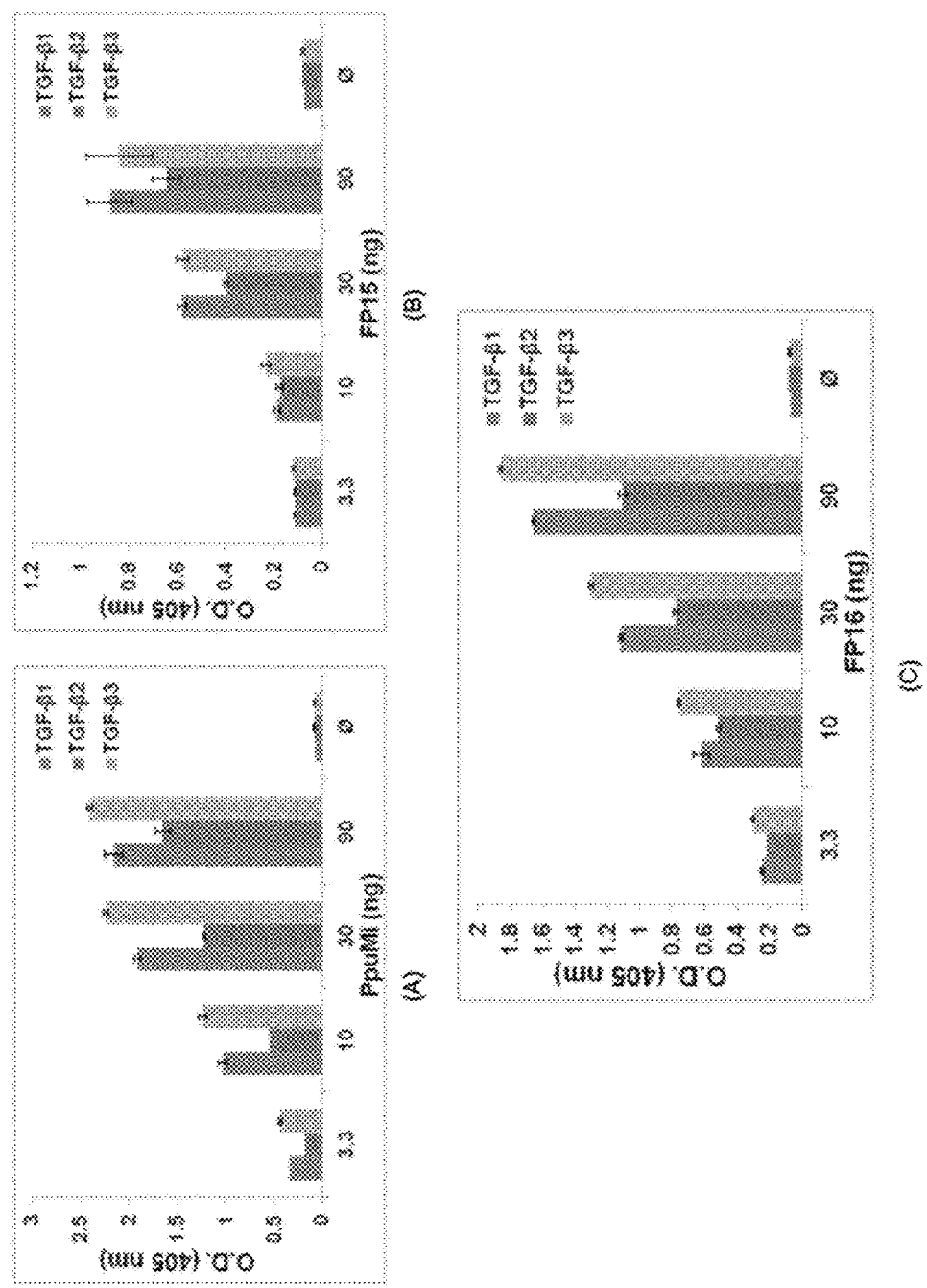
FIG. 9 shows the dose-dependent binding of PCR3 and PCR2 subdomains to all three TGF-βs.

FIG. 9 shows the dose-dependent binding of PCR3 and PCR2 subdomains to all three TGF-βs. As shown in FIG. 9, ELISA plates were coated with either of the TGF-β isoforms and then incubated with the indicated amounts of either PpuMi, FP15, FP16 or no protein. Note that there was a dose-dependent interaction between all three NC1 subfragments and all isoforms of TGF-β. These results further support the presence of two binding sites within the NC1 domain of Collagen 7 for all forms of TGF-β.

Figure 10:
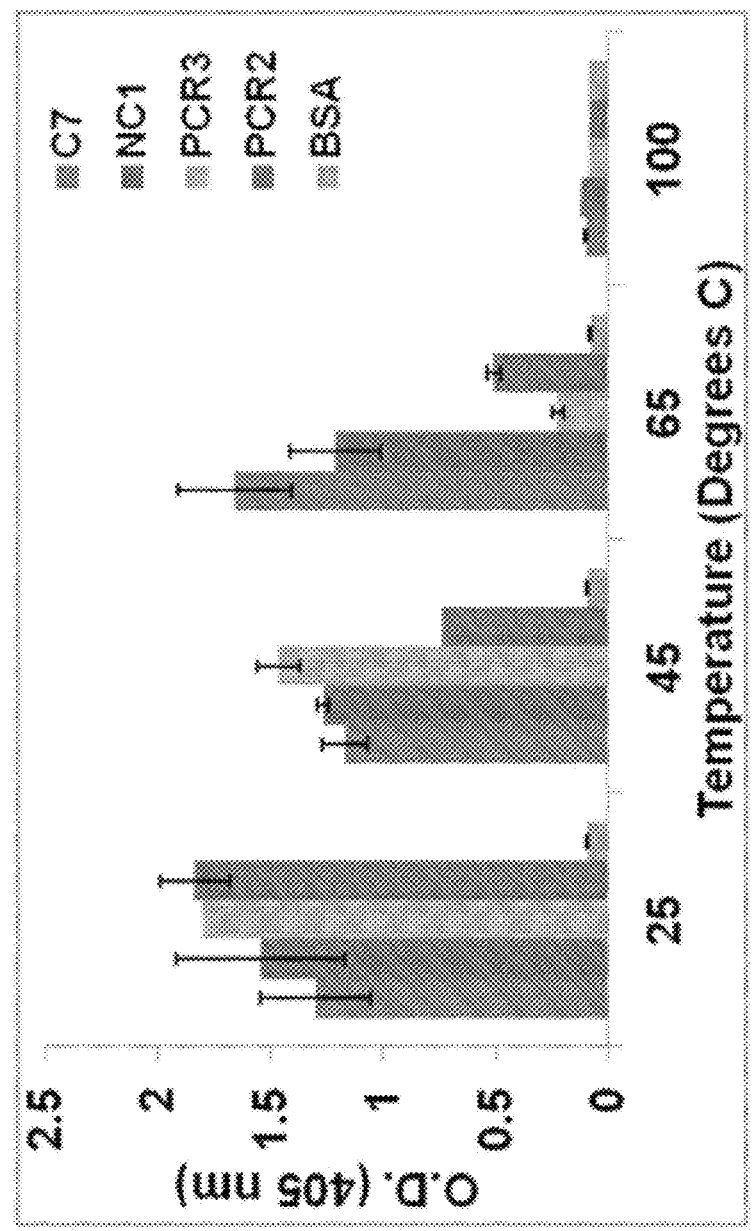
FIG. 10 shows that TGF-β1 binding to Collagen 7 and subdomains is temperature sensitive.

FIG. 10 shows that TGF-β1 binding to Collagen 7 and subdomains is temperature sensitive. ELISA plates were coated with TGF-β1 and then incubated with the equivalent molar amounts of indicated proteins that were pretreated for 5 minutes at the temperatures indicated above. Note that the smaller subdomains loss their TGF-β1 binding activity at temperatures 65° C. or above. In contrast, Collagen 7 and NC1 are more resistant to temperature inactivation and loss their binding activity at 100° C.

Example 10. C7 Binds More Strongly to TGF-β than Fibronectin

Figure 11:
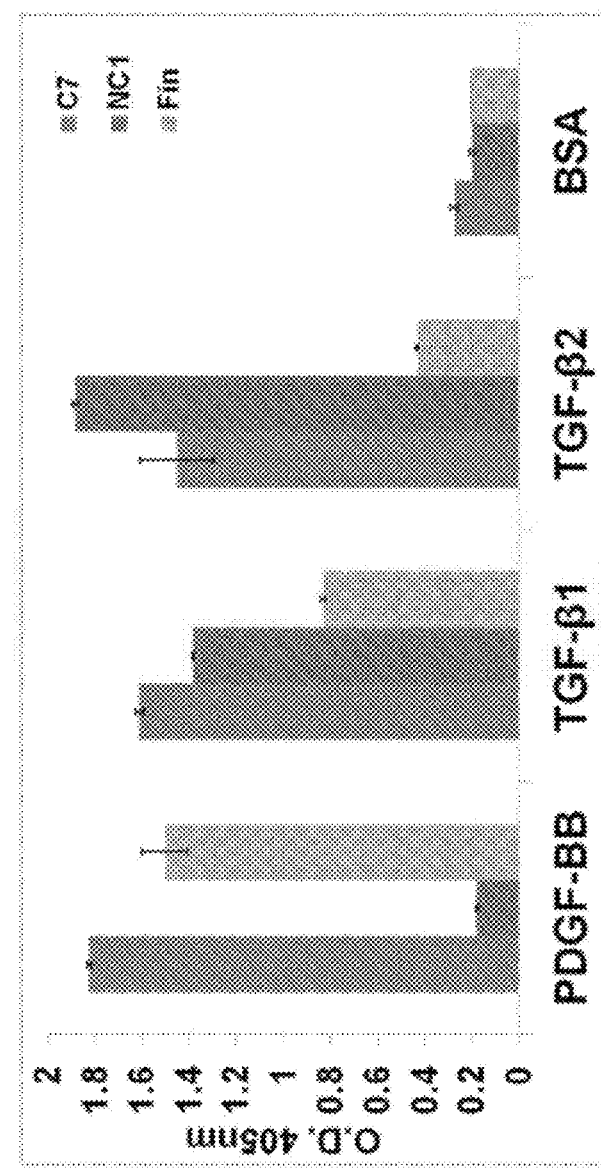
As shown in FIG. 11, we compared the binding of fibronectin and rC7 to TGF beta isoforms and the growth factor, PDFG-BB. Please note that C7 and NC1 bind significantly stronger to TGF beta 1 and 2 than fibronectin. There is no significant difference in the binding to PDGF-BB between C7 and fibronectin.

Fibronectin is also known to bind to TGF beta isoforms. FIG. 11 compares the binding of fibronectin and rC7 to TGF beta isoforms and the growth factor, PDFG-BB. Please note that C7 and NC1 bind significantly stronger to TGF beta 1 and 2 than fibronectin. Interestingly, there is no significant difference in the binding to PDGF-BB between C7 and fibronectin. FIG. 11A shows Coomassive Blue stained 6% SDS-PAGE slab gel of the purified recombinant NC1, fibronectin and C7 used in this experiment.

Figure 12:
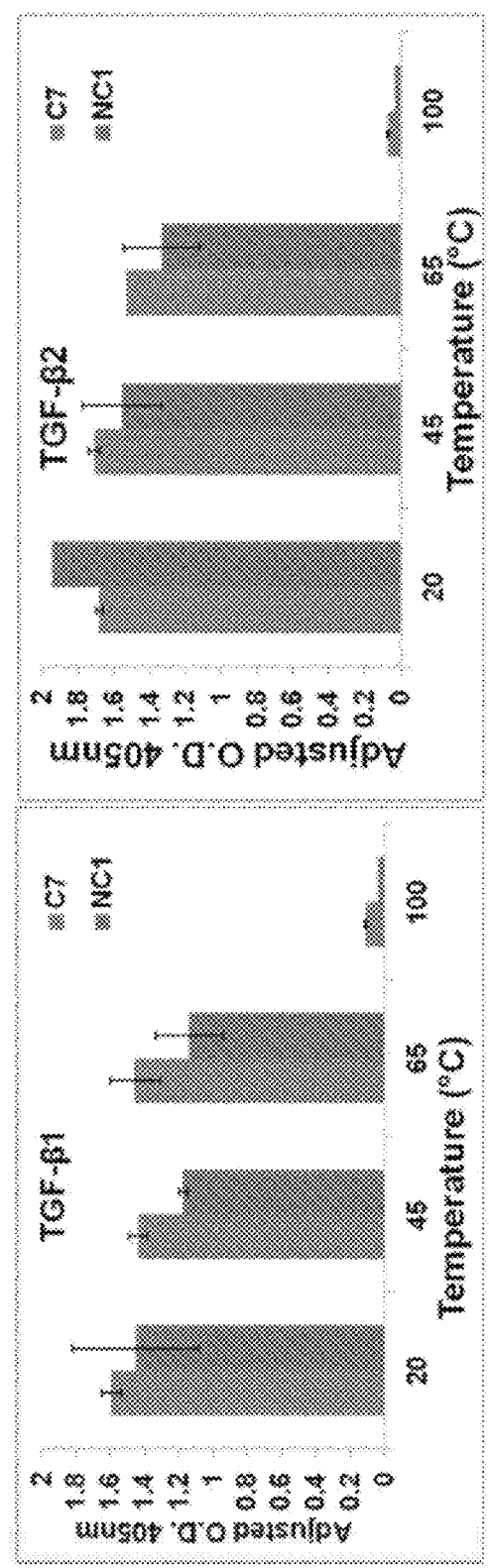
FIGS. 12A and 12B show C7 and NC1's ability to bind TGF-β1 and TGF-β2 Is retained with elevated temperature. One measure of the strength of protein to protein binding interactions is the persistence of their affinity at high temperatures. In this experiment, C7 or NC1 was pre-incubated at 20, 45, 65 and 100 for 5 minutes and then added them to the binding assays.

Example 11: C7/NC1's Ability to Bind TGF-β1 and TGF-β2 is Retained with Elevated Temperature One measure of the strength of protein to protein binding interactions is the persistence of their affinity at high temperatures. As shown in FIG. 12, we pre-incubated C7 or NC1 at 20, 45, 65 and 100 for 5 minutes and then added them to the binding assays. As is shown in FIGS. 12A and 12B, the ability of rC7 and NC1 to bind to TGF-beta 1 and 2, respectively is retained at temperatures as high as 65 degree but loss it activity upon heating at 100 degree.

Example 12. TGF-β Isoforms Compete for Binding to NC1

In the experiment shown in FIG. 13A, we mixed recombinant NC1 with each TGF beta isoform and then performed immuno-precipitation with an anti-NC1 antibody. We then ran the precipitate out on a SDS-PAGE gel and performed a immunoblot using antibodies to each TGF beta isoform. Please note that in accordance with the antigen-to-antigen ELISA data, by immunoprecipitation, NC1 binds to all three TGF-beta isoform. As shown in FIG. 13B, we examined if NC1 utilizes the same binding site for all three TGF beta isoform by an antigen-to-antigen ELISA competition assay. Please note that binding of NC1 to TGF beta 1 was inhibited by 50% and by 90% by presence of 10-fold excesses of TGF-beta 2 and beta 3, respectively. These data indicate that the 3 TGF beta isoforms bind to the same site of NC1.

Figure 15:
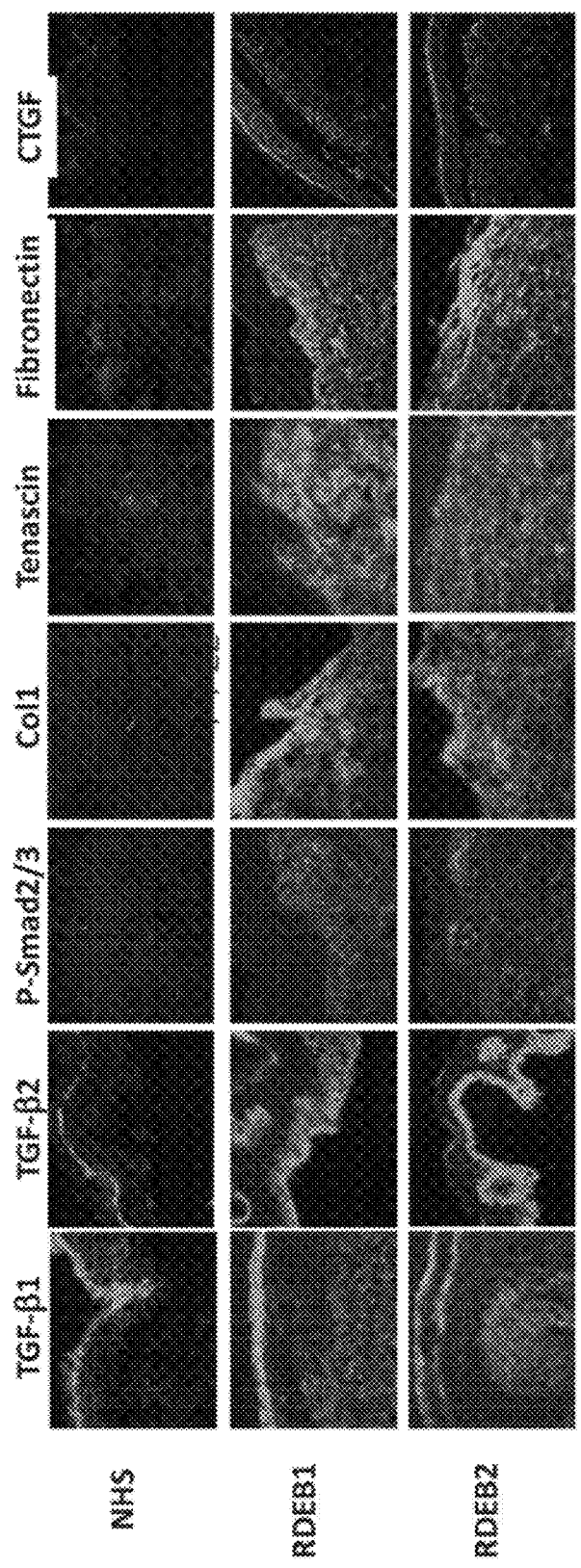
FIG. 15 shows IF staining of skin biopsies from two RDEB patients with antibodies to pro-fibrogenic isoforms of TGF-beta1 and 2 and antibodies to known markers of skin scarring. Note that compared with normal skin, the skin of RDEB patients exhibits increased expression of TGF beta 1, beta 2, p-Smad2/3 (a down stream element of TGF beta signaling), type I collagen, tenascin, fibronectin and CTGF, all markers of fibrosis and scarring.

Example 13: RDEB Patients' Skin have Increased Expression of Markers Associated with Fibrosis Since RDEB wounds heal with excessive scar formation, we performed IF staining of skin biopsies from two RDEB patients with antibodies to pro-fibrogenic isoforms of TGF-beta1 and 2 and antibodies to known markers of skin scarring. Note that compared with normal skin, as shown in FIG. 15 the skin of RDEB patients exhibits increased expression of TGF beta 1, beta 2, p-Smad2/3 (a down stream element of TGF beta signaling), type I collagen, tenascin, fibronectin and CTGF, all markers of fibrosis and scarring.

Example 14. Recombinant C7 Inhibits Growth Factor Induced FPCLC by RDEB Fibroblasts RDEB fibroblasts lack functional type VII collagen. We determined if the presence of recombinant type VII collagen could inhibit the hyper-contractability of collagen lattices of RDEB fibroblasts. As shown in FIG. 16, the addition of recombinant C7 to the collagen lattice contraction assays inhibited not only growth factor induced but also basal contraction of RDEB fibroblasts.

RDEB fibroblasts lack functional type VII collagen. We next determined if the presence of recombinant type VII collagen could inhibit the hyper-contractability of collagen lattices of RDEB fibroblasts. As shown in FIG. 17, the addition of recombinant C7 to the collagen lattice contraction assays inhibited not only growth factor induced but also basal contraction of RDEB fibroblasts.

Some Findings evident from these examples include:
RDEB patients' skin exhibit elevated levels of pro-fibrotic TGF-β1 and TGF-β2.
RDEB patients' fibroblast induce hypercontraction of collagen lattices compared with normal fibroblasts.
The presence of rC7 reverses RDEB-fibroblasts hyper-contraction of collagen lattices.
rC7 binds stronger to all 3 forms of TGF-β than fibronectin.
NC1 or C7 utilize the same binding sites for all three TGF-β isoforms.
rC7 binding to TGF-β is mediated via 2 sub-domains of NC1.

Certain Implications Flowing from the Result
Excessive scarring in RDEB may be due to intrinsic elevation of pro-fibrotic TGF-β isoforms in response to the absence of functional C7.
C7 itself may have anti-scarring properties via the mechanism of binding to pro-fibrotic TGF-β isoforms.
C7 or one of its anti-fibrotic sub-domains may have potential for development as an anti-scarring wound healing agent.

Materials and Methods
Construction and Expression of Collagen 7, NC1 and NC1 Subdomains:

Recombinant Collagen 7 was purified from serum free media from RDEB dermal fibroblasts stably transduced with a lentiviral vector coding for full-length Collagen 7 as described (Chen et al, 2004). The NC1 domain of Collagen 7 was purified from 293 cells stably transfected with cDNA encoding for NC1 as described (Chen et al, 1997). Bacterial fusion proteins corresponding to discrete segments within the NC1 domain of Collagen 7 were developed and purified by a glutathione-Sepharose 4B column (Pharmacia Uppsala, Sweden) as described (Lapiere et al, 1993).

Solid Phase Proteins Binding Assays:
Binding of soluble Collagen 7, NC1 and various subdomains of NC1 to immobilized ligands (TGF-β isoforms or other growth factors) followed by a colorimetric enzyme-linked antibody reaction was performed as described below. Multiwell plates (96 wells, Dynatech, Chantilly, Va.) were coated with TGF-β (125 ng per well) at 37° C. for one hour in 100 mM carbonate buffer, pH 9.3. The wells were then blocked with 2% bovine serum albumin (BSA) in phosphate-buffered saline, 0.05% Tween-20 (PBST). Coated wells were subsequently incubated with purified recombinant NC1, Collagen 7 or subdomains of NC1 at a concentrations indicated for 2 hours at room temperature. The binding of Collagen 7 to each TGF-β isoform was detected with a polyclonal anti-NC1 antibody or an antibody to GST, at a dilution of 1:2000 followed by incubation with alkaline phosphatase-conjugated goat anti-rabbit IgG (1:400) (Organon Teknika-Cappel, Durham, N.C.). The development of the colorimetric reaction using p-nitro-phenylphosphate as a substrate (Bio-Rad, Melville, N.Y.) was measured by reading the absorbance of the product at 405 nm (Labsystems Multiskan Multisoft, Finland). A control wavelength was measured at 620 nm.

---

COLLAGEN TYPE VII SEQUENCE INFORMATION

```
Name: Collagen alpha-1(VII) chain precursor [Homo sapiens]
NCBI Reference Sequence: NP_000085.1
FEATURES   Location/Qualifiers
   source  1..2944
           /organism="Homo sapiens"
           /db_xref="taxon:9606"
           /chromosome="3"
           /map="3p21.1"
   Protein 1..2944
           /product="collagen alpha-1(VII) chain precursor"
           /note="LC collagen; collagen VII, alpha-1 polypeptide;
           collagen alpha-1(VII) chain; long-chain collagen"
   sig_peptide 1..16
           /calculated_mol_wt=1629
   mat_peptide 17..2944
           /product="collagen alpha-1(VII) chain"
           /calculated_mol_wt=293610
```

-continued

| COLLAGEN TYPE VII SEQUENCE INFORMATION |
|---|

```
Region 17..1253
     /region_name="Nonhelical region (NC1)"
     /experiment="experimental evidence, no additional details
     recorded"
     /note="propagated from UniProtKB/Swiss-Prot (Q02388.2)"
Region 37..201
     /region_name="vWA_collagen_alPhaI-XII-like"
     /note="Collagen: The extracellular matrix represents a
     complex alloy of variable members of diverse protein
     families defining structural integrity and various
     physiological functions. The most abundant family is the
     collagens with more than 20 different...; cd01482"
     /db_xref="CDD:238759"
Site order (44,46,48,117,149)
     /site_type="other"
     /note="metal ion-dependent adhesion site (MIDAS)"
     /db_xref="CDD:238759"
Site order (46..48,50,117)
     /site_type="other"
     /note="integrin-collagen binding site"
     /db_xref="CDD:238759"
Region 233..325
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order (299,314)
     /site_type="other"
     /note="Interdomain contacts"
     /db_xref="CDD:238020"
Site order (315..316,318)
     /site_type="other"
     /note="Cytokine receptor motif"
     /db_xref="CDD:238020"
Region 333..413
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order (387,402)
     /site_type="other"
     /note="Interdomain contacts"
     /db_xref="CDD:238020"
Site order (403..404,405..406)
     /site_type="other"
     /note="Cytokine receptor motif'
     /db_xref="CDD:238020"
Region 419..492
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order(476,491)
     /site_type="other"
     /note="Interdomain contacts"
     /db_xref="CDD:238020"
Region 509..587
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order (567,582)
     /site_type="other"
     /note="Interdomain contacts"
     /db_xref="CDD:238020"
```

| COLLAGEN TYPE VII SEQUENCE INFORMATION |
| --- |

```
Site order (583..584,586..587)
     /site_type="other"
     /note="Cytokine receptor motif'
     /db_xref="CDD:238020"
Region 598..680
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately
     /db_xref="CDD:238020"2%
Site order (598,657,672)
     /site_type="other"
     /note="Interdomain contacts"
     /db_xref="CDD:238020"
Site order (673..674,676..677)
     /site_type="other"
     /note="Cytokine receptor motif'
     /db_xref="CDD:238020"
Region 687..771
     /region_name="FN3"
     inote="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order (745,760)
     /site_type="other"
     /note="Interdomain contacts"
     /db_xref="CDD:238020"
Site order (761..762,764..765)
     /site_type="other"
     /note="Cytokine receptor motif'
     /db_xref="CDD:238020"
Region 777..862
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order (836,851)
     /site_type="other"
     /note="Interdomain contacts"
     /db_xref="CDD:238020"
Site order(852..853,855..856)
     /site_type="other"
     inote="Cytokine receptor motif'
     /db_xref="CDD:238020"
Region 867..952
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
Site order (867,926,941)
     /site_type="other"
     /note="Interdomain contacts"
     /db_xref="CDD:238020"
Site order (942..943,944..945)
     /site_type="other"
     /note="Cytokine receptor motif'
     /db_xref="CDD:238020"
Region 955..1044
     /region_name="FN3"
     /note="Fibronectin type 3 domain; One of three types of
     internal repeats found in the plasma protein fibronectin.
     Its tenth fibronectin type III repeat contains an RGD cell
     recognition sequence in a flexible loop between 2 strands.
     Approximately 2% of all...; cd00063"
     /db_xref="CDD:238020"
```

COLLAGEN TYPE VII SEQUENCE INFORMATION

```
Site order (955,1020,1035)
     /site_type="other"
     /note="Interdomain contacts"
     /db_xref="CDD:238020"
Site order (1036..1037,1039..1040)
     /site_type="other"
     /note="Cytokine receptor motif'
     /db_xref="CDD:238020"
Region 1053..1204
     /region_name="vWFA_subfamily_ECM"
     /note="Von Willebrand factor type A (vWA) domain was
     originally found in the blood coagulation protein von
     Willebrand factor (vWF). Typically, the vWA domain is made
     up of approximately 200 amino acid residues folded into a
     classic a/b para-rossmann type of...; cd01450"
     /db_xref="CDD:238727"
Site order (1053,1055,1075,1160,1162,1188)
     /site_type="other"
     /note="integrin inhibitor binding pocket"
     /db_xref="CDD:238727"
Site order (1060,1062,1132,1166)
     /site_type="other"
     /note="metal ion-dependentadhesion site (MIDAS)"
     /db_xref="CDD:238727"
Site order (1062..1063,1064,1132)
     /site_type="other"
     /note="integrin-collagen binding site"
     /db_xref="CDD:238727"
Site order (1092,1107..1108,1119..1120)
     /site_type="other"
     /note="putative vWF-collagen binding site"
     /db_xref="CDD:238727"
Site order (1101..1102,1104,1136,1139,1143..1144)
     /site_type="other"
     /note="glycoprotein Ib (GpIb) binding site [polypeptide
     binding]"
     /db_xref="CDD:238727"
Region 1170..1172
     /region_name="Cell attachment site (Potential)"
     /inference="non-experimental evidence, no additional
     details recorded"
     /note="propagated fromUniProtKB/Swiss-Prot (Q02388.2)"
Region 1254..2784
     /region_name="Triple-helical region"
     /experiment="experimental evidence, no additional details
     recorded"
     /note="propagated from UniProtKB/Swiss-Prot (Q02388.2)"
Region 1254..1477
     /region_name="Interrupted collagenous region"
     /experiment="experimental evidence, no additional details
     recorded"
     /note="propagated from UniProtKB/Swiss-Prot (Q02388.2)"
Region 1299..1353
     /region_name="Collagen"
     inote="Collagen triple helix repeat (20 copies);
     pfam01391"
     /db_xref="CDD:189968"
Region 1334..1336
     /region_name="Cell attachment site (Potential)"
     /inference="non-experimental evidence, no additional
     details recorded"
     /note="propagated from UniProtKB/Swiss-Prot (Q02388.2)"
Region 1451..1504
     /region_name="Collagen"
     /note="Collagen triple helix repeat (20 copies);
     pfam01391"
     /db_xref="CDD:189968"
Region 1764..1816
     /region_name="Collagen"
     /note="Collagen triple helix repeat (20 copies);
     pfam01391"
     /db_xref="CDD:189968"
Region 2008..2010
     /region_name="Cell attachment site (Potential)"
     /inference="non-experimental evidence, no additional
     details recorded"
     /note="propagated from UniProtKB/Swiss-Prot(Q02388.2)"
```

COLLAGEN TYPE VII SEQUENCE INFORMATION

```
Region 2022..2074
     /region_name="Collagen"
     /note="Collagen triple helix repeat (20 copies);
     pfam01391"
     /db_xref="CDD:189968"
Region 2108..2166
     /region_name="Collagen"
     /note="Collagen triple helix repeat (20 copies);
     pfam01391"
     /db_xref="CDD:189968"
Site 2167
     /site_type="hydroxylation"
     /experiment="experimental evidence, no additional details
     recorded"
     /note="4-hydroxyproline; propagated from
     UniProtKB/Swiss-Prot (Q02388.2)"
Site 2176
     /site_type="hydroxylation"
     /experiment="experimental evidence, no additional details
     recorded"
     /note="4-hydroxyproline; propagated from
     UniProtKB/Swiss-Prot(Q02388.2)"
Site 2185
     /site_type="hydroxylation"
     /experiment="experimental evidence, no additional details
     recorded"
     /note="4-hydroxyproline; propagated from
     UniProtKB/Swiss-Prot (Q02388.2)"
Site 2188
     /site_type="hydroxylation"
     /experiment" experimental evidence, no additional details
     recorded"
     /note="4-hydroxyproline; propagated from
     UniProtKB/Swiss-Prot (Q02388.2)"
Region 2242..2301
     /region_name="Collagen"
     /note="Collagen triple helix repeat (20 copies);
     pfarn01391"
     /db_xref="CDD:189968"
Region 2324..2369
     /region_name="Collagen"
     /note="Collagen triple helix repeat (20 copies);
     pfam01391"
     /db_xref="CDD:189968"
Region 2466..2520
     /region_name="Collagen"
     /note="Collagen triple helix repeat (20 copies);
     pfam01391"
     /db_xref="CDD:189968"
Region 2527..2598
     /region_name="Collagen"
     /note="Collagen triple helix repeat (20 copies);
     pfam01391"
     /db_xref="CDD:189968"
Region 2553..2555
     /region_name="Cell attachment site (Potential)"
     /inference="non-experimental evidence, no additional
     details recorded"
     /note="propagated from UniProtKB/Swiss-Prot (Q02388.2)"
Region 2614..2673
     /region_name="Collagen"
     /note="Collagen triple helix repeat (20 copies);
     pfam01391"
     /db_xref="CDD:189968"
Site 2625
     /site_type="hydroxylation"
     /experiment" experimental evidence, no additional details
     recorded"
     /note="5-hydroxylysine, alternate; propagated from
     UniProtKB/Swiss-Prot(Q02388.2)"
Site 2631
     /site_type="hydroxylation"
     /experiment="experimentalevidence, no additional details
     recorded"
     /note="5-hydroxylysine, alternate; propagated from
     UniProtKB/Swiss-Prot (Q02388.2)"
```

COLLAGEN TYPE VII SEQUENCE INFORMATION

```
Region   2650..2707
         /region_name="Collagen"
         /note="Collagen triple helix repeat (20 copies);
         pfam01391"
         /db_xref="CDD:189968"
Site     2664
         /site_type="hydroxylation"
         /experiment="experimental evidence, no additional details
         recorded"
         /note="4-hydroxyproline; propagated from
         UniProtKB/Swiss-Prot(Q02388.2)"
Site     2667
         /site_type="hydroxylation"
         /experiment="experimental evidence, no additional details
         recorded"
         /note="4-hydroxyproline;propagated from
         UniProtKB/Swiss-Prot(Q02388.2)"
Site     2673
         /site_type="hydroxylation"
         /experiment="experimental evidence, no additional details
         recorded"
         /note="4-hydroxyproline; propagated from
         UniProtKB/Swiss-Prot (Q02388.2)"
Region   2785..2944
         /region_name="Nonhelical region (NC2)"
         /experiment="experimental evidence, no additional details
         recorded"
         /note="propagated from UniProtKB/Swiss-Prot (Q02388.2)"
Site     2821
         /site_type="modified"
         /experiment" experimental evidence, no additional details
         recorded"
         /note="proteolytic cleavage site"
         /citation=[6]
         /db_xref="HPRD:00209"
Region   2874..2930
         /region_name="KU"
         /note="BPTI/Kunitz family of serine protease inhibitors;
         Structure is a disulfide rich alpha+beta fold. BPTI
         (bovine pancreatic trypsin inhibitor) is an extensively
         studied model structure; cd00109"
         /db_xref="CDD:238057"
Site     order 2884..2888,2890)
         /site_type="other"
         /note="trypsin interaction site"
         /db_xref="CDD:238057"
Site     2886..2887
         isite_type="other"
         /inference="non-experimental evidence, no additional
         details recorded"
         /note="Reactive bond (By similarity); propagated from
         UniProtKB/Swiss-Prot (Q02388.2)"
CDS      1..2944
         /gene="COL7A1"
         /gene_synonym="EBD1; EBDCT; EBR1"
         /coded_by="NM_000094.3:2..8836"
         /db_xref="CCDS:CCDS2773.1"
         /db_xref="GeneID:1294"
         /db_xref="HGNC:2214"
         /db_xref="HPRD:00358"
         /db_xref="MIM:120120"

ORIGIN (SEQ ID NO: 1)
    1 mtlrllvaal cagilaeapr vraqhrervt ctrlyaadiv flldgsssig rsnfrevrsf
   61 leglvlpfsg aasaqgvrfa tvqysddprt efgldalgsg gdvirairel sykggntrtg
  121 aailhvadhv flpqlarpgv pkvcilitdg ksqdlvdtaa qrlkgqgvkl favgiknadp
  181 eelkrvasqp tsdffffvnd fsilrtllpl vsrrvcttag gvpvtrppdd stsaprdlvl
  241 sepssqslry qwtaasgpvt gykvqytplt glgqplpser qevnvpaget svrlrglrpl
  301 teyqvtvial yansigeavs gtarttaleg peltiqntta hsllvawrsv pgatgyrvtw
  361 rvlsggptqq qelgpgqgsv llrdlepgtd yevtvstlfg rsvgpatslm artdasveqt
  421 lrpvilgpts illswnlvpe argyrlewrr etgleppqkv vlpsdvtryq ldglqpgtey
  481 rltlytlleg hevatpatvv ptgpelpvsp vtdlqatelp gqrvrvswsp vpgatqyrii
  541 vrstqgvert lvlpgsqtaf dlddvqagls ytvrvsarvg pregsasvit vrrepetpla
  601 vpglrvvvsd atrvrvawgp vpgasgfris wstgsgpess qtlppdstat ditglqpgtt
  661 yqvaysvlrg reegpaaviv artdplgpvr tvhvtqasss svtitwtrvp gatgyrvswh
  721 sahgpeksql vsgeatvael dglepdteyt vhvrahvagv dgppasvvvr tapepvgrvs
  781 rlqilnassd vlritwvgvt gatayrlawg rseggpmrhq ilpgntdsae irgleggvsy
```

COLLAGEN TYPE VII SEQUENCE INFORMATION

```
 841 svrvtalvgd regtpvsivv ttppeappal gtlhvvqrge hslrlrwepv praqgfllhw
 901 qpeggqeqsr vlgpelssyh ldglepatqy rvrlsvlgpa gegpsaevta rtesprvpsi
 961 elrvvdtsid svtlawtpvs rassyilswr plrgpgqevp gspqtlpgis ssqrvtglep
1021 gvsyifsltp vldgvrgpea svtqtpvcpr gladvvflph atqdnahrae atrrvlerlv
1081 lalgplgpqa vqvgllsysh rpsplfplng shdlgiilqr irdmpymdps gnnlgtavvt
1141 ahrymlapda pgrrqhvpgv myllvdeplr gdifspirea qasglnvvml gmagadpeql
1201 rrlapgmdsv qtffavddgp sldqaysgla talcqasftt qprpepcpvy cpkgqkgepg
1261 emglrgqvgp pgdpglpgrt gapgpqgppg satakgergf pgadgrpgsp gragnpgtpg
1321 apglkgspgl pgprgdpger gprgpkgepg apgqviggeg pglpgrkgdp gpsgppgprg
1381 plgdpgprgp pglpgtamkg dkgdrgergp pgpgeggiap gepglpglpg spgpqgpvgp
1441 pgkkgekgds edgapglpgq pgspgeqgpr gppgaigpkg drgfpgplge agekgergpp
1501 gpagsrglpg vagrpgakgp egppgptgrq gekgepgrpg dpavvgpava gpkgekgdvg
1561 pagprgatgv qgergpplv lpgdpgpkgd pgdrgpiglt gragppgdsg ppgekgdpgr
1621 pgppgpvgpr grdgevgekg degppgdpgl pgkagerglr gapgvrgpvg ekgdqgdpge
1681 dgrngspgss gpkgdrgepg ppgppgrlvd tgpgarekge pgdrgqegpr gpkgdpglpg
1741 apgergiegf rgppgpqgdp gvrgpagekg drgppglpgr sgldgkpgaa gpsgpngaag
1801 kagdpgrdgl pglrgeqglp gpsgppglpg kpgedgkpgl ngkngepgdp gedgrkgekg
1861 dsgasgregr dgpkgergap gilgpqgppg lpgpvgppgq gfpgvpggtg pkgdrgetgs
1921 kgeqglpger glrgepgsvp nvdrlletag ikasalreiv etwdessgsf lpvperrrgp
1981 kgdsgeqgpp gkegpigfpg erglkgdrgd pgpqgppgla lgergppgps glagepgkpg
2041 ipglpgragg vgeagrpger gergekgerg eqgrdgppgl pgtpgppgpp gpkvsvdepg
2101 pglsgeqgpp glkgakgepg sngdqgpkgd rgvpgikgdr gepgprgqdg npglpgergm
2161 agpegkpglq gprgppgpvg ghgdpgppga pglagpagpq gpsglkgepg etgppgrglt
2221 gptgavglpg ppgpsglvgp qgspglpgqv getgkpgapg rdgasgkdgd rgspgvpgsp
2281 glpgpvgpkg epgptgapgq avvglpgakg ekgapgglag dlvgepgakg drglpgprge
2341 kgeagragep gdpgedgqkg apgpkgfkgd pgvgvpgspg ppgppgvkgd lglpglpgap
2401 gvvgfpgqtg prgemgqpgp sgerglagpp gregipgplg ppgppgsvgp pgasglkgdk
2461 gdpgvglpgp rgergepgir gedgrpgqeg prgltgppgs rgergekgdv gsaglkgdkg
2521 dsavilgppg prgakgdmge rgprgldgdk gprgdngdpg dkgskgepgd kgsaglpglr
2581 gllgpqgqpg aagipgdpgs pgkdgvpgir gekgdvgfmg prglkgergv kgacgldgek
2641 gdkgeagppg tpglaghkge mgepgvpgqs gapgkeglig pkgdrgfdgq pgpkgdqgek
2701 gergtpgigg fpgpsgndgs agppgppgsv gprgpeglqg qkgergppge rvvgapgvpg
2761 apgergeqgr pgpagprgek geaalteddi rgfvrqemsq hcacqgqfia sgsrplpsya
2821 adtagsqlha vpvlrvshae eeervppedd eyseyseysv eeyqdpeapw dsddpcslpl
2881 degsctaytl rwyhravtgs teachpfvyg gcggnanrfg treacerrcp prvvqsqgtg
2941 taqd
//
```

PCR2 (AA 596-826 of SEQ ID NO: 1)
ETPLAVPGLRVVVSDATRVRVAWGPVPGASGFRISWSTGSGPESSQTLPPDSTAT
DITGLQPGTTYQVAVSVLRGREEGPAAVIVARTDPLGPVRTVHVTQASSSSVTITWTRVP
GATGYRVSWHSAHGPEKSQLVSGEATVAELDGLEPDTEYTVHVRAHVAGVDGPPASV
VVRTAPEPVGRVSRLQILNASSDVLRITWVGVTGATAYRLAWGRSEGGPMRHQILPGNT

PCR3 (AA 202-602 of SEQ ID NO: 1)
SILRTLLPLVSRRVCTTAGGVPVTRPPDDSTSAPRDLVLSEPSSQSLRVQWTAASG
PVTGYKVQYTPLTGLGQPLPSERQEVNVPAGETSVRLRGLRPLTEYQVTVIALYANSIGE
AVSGTARTTALEGPELTIQNTTAHSLLVAWRSVPGATGYRVTWRVLSGGPTQQQELGP
GQGSVLLRDLEPGTDYEVTVSTLFGRSVGPATSLMARTDASVEQTLRPVILGPTSILLSW
NLVPEARGYRLEWRRETGLEPPQKVVLPSDVTRYQLDGLQPGTEYRLTYTLLEGHEV
ATPATVVPTGPELPVSPVTDLQATELPGQRVRVSWSPVPGATQYRIIVRSTQGVERTLVL
PGSQTAFDLDDVQAGLSYTVRVSARVGPREGSASVLTVRRREPETPLAVP

PpuMi (AA 202-360 of SEQ ID NO: 1)
SILRTLLPLVSRRVCTTAGGVPVTRPPDDSTSAPRDLVLSEPSSQSLRVQWTAASG
PVTGYKVQYTPLTGLGQPLPSERQEVNVPAGETSVRLRGLRPLTEYQVTVIALYANSIGE
AVSGTARTTALEGPELTIQNTTAHSLLVAWRSVPGATGYRVTW

FP15 (AA 596-709 of SEQ ID NO: 1)
ETPLAVPGLRVVVSDATRVRVAWGPVPGASGFRISWSTGSGPESSQTLPPDSTAT
DITGLQPGTTYQVAVSVLRGREEGPAAVIVARTDPLGPVRTVHVTQASSSSVTITWTRV

FP16 (AA 707-826 of SEQ ID NO: 1)
TRVPGATGYRVSWHSAHGPEKSQLVSGEATVAELDGLEPDTEYTVHVRAHVAG
VDGPPASVVVRTAPEPVGRVSRLQILNASSDVLRITWVGVTGATAYRLAWGRSEGGPM
RHQILPGNT

The invention claimed is:

1. An isolated polypeptide comprising one or more functional fragments of collagen 7, wherein collagen 7 has an amino acid sequence as set forth in SEQ ID NO:1, and wherein the one or more functional fragments is selected from the group consisting of FNIII Region 1 having an amino acid sequence corresponding to amino acid residues 233 to 325 of SEQ ID NO:1, FNIII Region 2 having an amino acid sequence corresponding to amino acid residues 333 to 413 of SEQ ID NO:1, FNIII Region 3 having an amino acid sequence corresponding to amino acid residues 419 to 492 of SEQ ID NO:1, FNIII Region 4 having an amino acid sequence corresponding to amino acid residues 509 to 587 of SEQ ID NO:1, FNIII Region 5 having an amino acid sequence corresponding to amino acid residues 598 to 680 of SEQ ID NO:1, FNIII Region 6 having an amino acid sequence corresponding to amino acid residues 687 to 771 of SEQ ID NO:1, FNIII Region 7 having an amino acid sequence corresponding to amino acid residues 777 to 862 of SEQ ID NO:1, FNIII Region 8 having an amino acid sequence corresponding to amino acid residues 867 to 952 of SEQ ID NO:1, FNIII Region 9 having an amino acid sequence corresponding to amino acid residues 955 to 1044 of SEQ ID NO:1, PCR2 having an amino acid sequence corresponding to amino acid residues 596 to 826 of SEQ ID NO:1, PCR3 having an amino acid sequence corresponding to amino acid residues 202 to 602 of SEQ ID NO:1, FP15 having an amino acid sequence corresponding to amino acid residues 596 to 709 of SEQ ID NO:1, FP16 having an amino acid sequence corresponding to amino acid residues 707 to 826 of SEQ ID NO:1, and PpuMi having an amino acid sequence corresponding to amino acid residues 202 to 360 of SEQ ID NO:1.

2. The isolated polypeptide according to claim 1, wherein the isolated polypeptide is not capable of forming anchoring fibrils between the epidermal and dermal layers of human skin but is capable of binding to TGF-β1 and inhibiting TGF-β1 and TGF-β2 activity.

3. The isolated polypeptide according to claim 1, wherein the one or more functional fragments is selected from the group consisting of FNIII Region 1, FNIII Region 2, FNIII Region 3, FNIII Region 4, FNIII Region 5, FNIII Region 6, FNIII Region 7, FNIII Region 8, and FNIII Region 9.

4. The isolated polypeptide according to claim 3, wherein the isolated polypeptide comprises an amino acid sequence corresponding to residues 17 to 1253 of SEQ ID NO:1.

5. The isolated polypeptide according to claim 4, wherein the isolated polypeptide further comprises an amino acid sequence corresponding to a fragment of less than 100, 50, 40, 20 or 10 amino acid residues of the central collagenous helical domain and/or less than 40, 20 or 10 amino acid residues of the carboxy terminal NC2 domain.

6. The isolated polypeptide according to claim 1, wherein the one or more functional fragments is FNIII Region 1.

7. The isolated polypeptide according to claim 1, wherein the one or more functional fragments is FNIII Region 5.

8. The isolated polypeptide according to claim 1, wherein the one or more functional fragments is FNIII Region 6.

9. The isolated polypeptide according to claim 1, wherein the one or more functional fragments is PCR2.

10. The isolated polypeptide according to claim 1, wherein the one or more functional fragments is PCR3.

11. The isolated polypeptide according to claim 1, wherein the one or more functional fragments is FP15.

12. The isolated polypeptide according to claim 1, wherein the one or more functional fragments is FP16.

13. The isolated polypeptide according to claim 1, wherein the isolated polypeptide includes one or more amino acid sequences that correspond to the binding site of collagen 7 to TGF-β1 and/or TGF-β2.

14. A pharmaceutical composition comprising: one or more isolated polypeptides according to any one of claims 1-5, 6-8 or 9-13; and a pharmaceutical carrier.

* * * * *